(12) United States Patent
Rubessa et al.

(10) Patent No.: US 11,774,454 B2
(45) Date of Patent: Oct. 3, 2023

(54) NON-INVASIVE ANALYSIS OF EMBRYO METABOLITES

(71) Applicant: THE BOARD OF TRUSTEES OF THE UNIVERSITY OF ILLINOIS, Urbana, IL (US)

(72) Inventors: Marcello Rubessa, Champaign, IL (US); Matthew B. Wheeler, Tolono, IL (US); Andrea Ambrosi, Urbana, IL (US); Scott E. Denmark, Champaign, IL (US); Dianelys Gonzalez-Pena, Kalamazoo, MI (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 17/001,094

(22) Filed: May 12, 2023

(65) Prior Publication Data

US 2021/0055303 A1 Feb. 25, 2021

Related U.S. Application Data

(60) Provisional application No. 62/891,362, filed on Aug. 25, 2019.

(51) Int. Cl.
| | |
|---|---|
| *G01N 33/68* | (2006.01) |
| *G01N 33/50* | (2006.01) |
| *G01N 33/483* | (2006.01) |
| *A01K 45/00* | (2006.01) |

(52) U.S. Cl.
CPC ......... *G01N 33/6812* (2013.01); *A01K 45/00* (2013.01); *G01N 33/4833* (2013.01); *G01N 33/5091* (2013.01)

(58) Field of Classification Search
CPC ........... G01N 33/6812; G01N 33/4833; G01N 33/5091; A01K 45/00
See application file for complete search history.

(56) References Cited

U.S. PATENT DOCUMENTS

| 9,157,550 B2 | 10/2015 | Wheeler et al. |
| 2015/0260704 A1 | 9/2015 | Bruins et al. |

OTHER PUBLICATIONS

Bellver et al. "Day-3 embryo metabolomics in the spent culture media is altered in obese women undergoing in vitro fertilization" Fertility & Sterility 2015 103:1407 (Year: 2015).*
Gomez et al. "Differential release of cell-signaling metabolites by male and female bovine embryos cultured in vitro" 2018 Theriogenology 114: 180 (Year: 2018).*
Shamonki et al. "Proof of concept: preimplantation genetic screening without embryo biopsy through analysis of cell-free DNA in spent embryo culture media" 2016 Fertility and Sterility 106:1312 (Year: 2016).*
Alomar et al, "Kinetics of fertilization and development, and sex ratio of bovine embryos using the semen of different bulls", Animal Reproduction Science, vol. 107, No. 1-2, pp. 48-61, Aug. 2008.
Avery et al, "Impact of asynchronous ovulations on the expression of sex-dependent growth rate in bovine preimplantation embryos", Journal of Reproduction and Fertility, vol. 87, No. 2, pp. 627-631, Nov. 1989.
Avery et al, "Sex and development in bovine in-vitro fertilized embryos", Theriogenology, vol. 35, No. 5, pp. 953-963, May 1991.
Beebe et al, "Microfluidic technology for assisted reproduction", Theriogenology, vol. 57, No. 1, pp. 125-135, Jan. 1, 2002.
Carvalho et al, "Survival rates and sex ratio of bovine IVE embryos frozen at different developmental stages on day 7", Theriogenology, vol. 45, No. 2, pp. 489-498, Jan. 15, 1996.
Daneau et al, "Bovine SRY Gene Locus: Cloning and Testicular Expression", Biology of Reproduction, vol. 52, No. 3, pp. 591-599, Mar. 1, 1995.
Gomez et al, "Non-invasive metabolomics for improved determination of embryonic sex markers in chemically defined culture medium", Journal of Chromatography, vol. 1474, pp. 138-144, Nov. 25, 2016.
King et al, "The sex ratios of bovine embryos produced in vivo and in vitro", Theriogenology, vol. 36, No. 5, pp. 779-788, Nov. 1991.
Lindon et al, "Contemporary issues tn toxicology the role of metabonomics in toxicology and its evaluation by the COMET project", Toxicology and Applied Pharmacology, vol. 187, No. 3, pp. 137-146, Mar. 15, 2003.
MacIntyre et al, "Characterisation of Human Embryonic Stem-Cells Conditioning Media by 1H-Nuclear Magnetic Resonance Spectroscopy", PLoS One, vol. 6, No. 2, pp. e16732, Feb. 9, 2011.
Munoz et al, "Non-invasive assessment of embryonic sex in cattle by metabolic fingerprinting of in vitro culture medium", Metabolomics, vol. 10, pp. 443-451, (2014).
Nadal-Desbarats et al, "Is NMR metabolic profiling of spent embryo culture media useful to assist in vitro human embryo selection?", Magnetic Resonance Materials in Physics, Biology and Medicine, vol. 26, No. 2, pp. 193-202, (2013).
Parrish et al, "Bovine in vitro fertilization with frozen-thawed semen", Theriogenology, vol. 25, No. 4, pp. 591-600, Apr. 1986.
Raty et al, "Embryonic development in the mouse is enhanced microchannel culture", Lab on a Chip, vol. 4, pp. 186-190, Mar. 18, 2004.
Rubessa et al, "Non-invasive analysis of bovine embryo metabolites during in vitro embryo culture using nuclear magnetic resonance", AIMS Bioengineering, vol. 3, No. 4, pp. 538-551, Dec. 13, 2016.
Rubessa et al, "Non-Invasive Analysis of Gamete Metabolites During In Vitro Embryo Production Using Nuclear Magnetic Resonance", International Journal of New Technology, vol. 2, No. 3, pp. 54-58, Mar. 2016.
Rubessa et al, "Non-invasive nuclear magnetic resonance analysis of male and female embryo metabolites during in vitro embryo culture", Metabolomics, vol. 14, No. 113, pp. 1-9, (2018).
Sattar et al, "The Influence of Gamete Co-incubation Length on the In Vitro Fertility and Sex Ratio of Bovine Bulls with Different Penetration Speed", Reproduction in Domestic Animals, vol. 46. No. 6, pp. 1090-1097, Dec. 2011.

(Continued)

*Primary Examiner* — Changhwa J Cheu
(74) *Attorney, Agent, or Firm* — Lathrop GPM LLP; Lisa Hillman

(57) ABSTRACT

The present disclosure provides non-invasive methods for determining the gender of an embryo during in vitro embryo culture.

11 Claims, 11 Drawing Sheets
Specification includes a Sequence Listing.

(56) References Cited

OTHER PUBLICATIONS

Sturmey et al, "Amino Acid Metabolism of Bovine Blastocysts: A Biomarker of Sex and Viability", Molecular Research & Development, vol. 77, pp. 285-296, (2010).
Tervit et al, "Successful Culture In Vitro of Sheep and Cattle Ova", Journal of Reproduction and Fertility, vol. 30, No. 3, pp. 493-497, Sep. 1972.
Vajta et al, "The Well-of-the-Well System: an efficient approach to improve embryo development", Reproductive BioMedicine Online, vol. 17, No. 1, pp. 73-81, (2008).
Wallace et al, "1H NMR based metabolic profiling of day 2 spent embryo media correlates with implantation potential", Systems Biology in Reproductive Medicine, vol. 60, No. 1, (2014).
Yadav et al, "Relationships between the completion of first cleavage and the chromosomal complement, sex, and development rates of bovine embryos generated in vitro", Molecular Reproduction and Development, vol. 36, No. 4, pp. 434-439, Dec. 1993.

\* cited by examiner

NON-INVASIVE ANALYSIS OF EMBRYO METABOLITES

PRIORITY

This application claims the benefit of U.S. Ser. No. 62/891,362 filed on Aug. 25, 2019, the contents of which are incorporated by reference in their entirety.

FIELD

The present disclosure provides non-invasive methods for determining the gender of an embryo by metabolite analysis in vitro.

BACKGROUND

The in vitro production of bovine embryos has dramatically increased in recent years, representing approximately 66% of embryos transferred in the world (Guimarães et al. 2014, *Animal Reproduction Science*, 146(3-4):103-110). In 2011, the number of IVP (in vitro production) embryos produced and transferred were 453,471 and 373,836, respectively, worldwide (Parrish 2014 *Theriogenology*, 81(1):67-73). The most recent International Embryo Transfer Society (IETS) data report indicates that in 2014, 1,206,914 embryos were produced (in vivo and in vitro) and of these, 830,207 were transferred worldwide (Perry 2015 IETS, 2015 ed., pp. 9-11)). In the past 10 years, the number of transferred in vitro-produced embryos has continuously increased, to the point of approximating the annual number of in vivo-produced bovine embryos transferred (Hasler 2014 *Theriogenology*, 81(1):152-169). In a review, Hasler (2014) stated that in the last 10 years the number of in vitro embryo transfers has continuously increased, even surpassing the annual number of embryo transfers from in vivo-produced embryos. This growth in embryo production (given the massive demand) drives research to deepen understanding of the metabolic behavior during embryonic development in order to try to increase embryo production. Studies to improve embryo production also evaluated differences between male and female embryo development. In summary, previous studies have shown that male embryos develop faster in vitro than female embryos (Carvalho et al. 1996 *Theriogenology*, 45(2): 489-498; Yadav et al. 1993 *Molecular Reproduction and Development*, 36(4): 434-439). These studies supported previous studies from Avery et al. where they demonstrated that this different speed of development is seen only in vitro (Avery et al. 1991, *Theriogenology*, 35(5): 953-963) and not in vivo (Avery 1989, *Journal of Reproduction and Fertility*, 87(2): 627-631).

Furthermore, in the past 20+ years, several studies of bovine embryo production showed how the ratio of male to female embryos changes if embryos are made in vivo versus in vitro. In 1991, King et al. (1991), *Theriogenology*, 36(5): 779-788 showed that the in vivo ratio between male and female embryos produced was 1:1. On the other hand, the sex ratio of in vitro systems can be manipulated to generate either male or female embryos.

Reproductive inefficiency is a major problem facing the beef and dairy industry. Additionally, freemartinism is one of the most severe forms of sexual abnormality in cattle, which can case infertility in the female calf born with a male twin sharing the same uterus. Gender determination of embryos before implantation can control incidence of freemartinism, as well as other sexual and genetic abnormalities in cattle. However, many of the current methods for gender determination are invasive and use PCR primers that target the sex chromosomes. Thus, there is a need for improved, non-invasive methods of gender determination, which can help increase, for example, meat and dairy production as well as conserve rare animal breeds.

Additionally, certain genetic diseases are associated with one sex. Patients, e.g., human patients, that are carriers for such diseases may not want a child with that sex if it has a chance to carry a sex-linked disease. The current method for screening requires microsurgery of the embryo, which decreases the viability and pregnancy rate of that embryo. Methodologies are needed for non-invasive determination of the embryo sex, which would allow a decision on whether to transfer that embryo.

BRIEF SUMMARY OF THE DISCLOSURE

The present disclosure relates to non-invasive methods for determining the gender of an embryo.

An embodiment provides a method for determining the gender of an embryo.

The method can comprise growing an embryo in an in vitro culture media; and identifying one or more metabolites contained in the spent culture media during early development, mid-development, late development, or a combination thereof, wherein the presence of one or more metabolites at a concentration that varies from a baseline concentration indicates the gender of the embryo. Early development can be about 1 day to about 3 days after a zygote is formed. Early development can be about 24 hours to about 72 hours after a zygote is formed. Mid-development can be about 3 days to about 5 days after a zygote is formed. Mid-development can be about 72 hours to about 120 hours after a zygote is formed. Late development can be about 5 days to about 7 days after a zygote is formed. Late development can be about 120 hours to about 168 hours after a zygote is formed. The embryo can be a human embryo, bovine embryo, a porcine embryo, an equine embryo, an ovine embryo, a hircine embryo, a canine embryo, a feline embryo, a murine embryo, a rabbit embryo, a chicken embryo, a carnivore embryo, a herbivore embryo, a rodent embryo, a bird embryo, or a mammalian embryo. The gender of the embryo can be determined before the embryo is transferred into an animal. The animal can be a human, cow, pig, horse, sheep, goat, dog, cat, mouse, rat, rabbit, or chicken. The one or more metabolites identified can be an amino acid, a sugar, or a nucleotide. The one or more metabolites identified can be formate, lactate, myo-inositol, citrate, pyruvate, acetate, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine or a combination thereof. In an embodiment the presence of the one or more metabolites indicates the gender of the embryo with an accuracy of over 60%.

In an embodiment, the presence of valine during early development in a concentration above a baseline indicates that an embryo will more likely be male than female. In another embodiment, the presence of valine during early development in a concentration below or about a baseline indicates that the embryo will more likely be female. In an embodiment, the presence of pyruvate during late development in a concentration at about or below a base line indicates that the embryo will more likely be female than male. In an embodiment, the presence of pyruvate during late development in a concentration above a baseline indicates that the embryo will more likely be male than female.

In an embodiment the metabolites are identified by nuclear magnetic resonance, high performance liquid chromatography, gas chromatography, or mass spectroscopy.

Yet another embodiment provides a method of determining a marker for gender evaluation of an embryo. The method comprises (i) growing an embryo in an in vitro culture media; (ii) identifying one or more metabolites contained in the spent culture media during early development, mid-development, and late development; (iii) comparing the concentrations of the one or more metabolites contained in the spent culture media during early development, mid-development, and late development to identify trends in the depletion of one or more metabolites during early development, mid-development, or late development; and (iv) correlating the depletion of one or more metabolites during early development, mid-development, or late development to the gender of the embryo. Early development can be about 1 day to about 3 days after a zygote is formed. Mid-development can be about 3 days to about 5 days after a zygote is formed. Late development can be about 5 days to about 7 days after a zygote is formed.

The embryo can be a human embryo, a bovine embryo, a porcine embryo, an equine embryo, an ovine embryo, a hircine embryo, a canine embryo, a feline embryo, a murine embryo, a rabbit embryo, or a chicken embryo. The one or more metabolites identified can be an amino acid, a sugar, or a nucleotide. The one or more metabolites identified can be formate, lactate, myo-inositol, citrate, pyruvate, acetate, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, or combinations thereof.

Trends in the depletion of the one or more metabolites during early development, mid-development, or late development can be identified by statistical analysis. Trends in the presence of the one or more metabolites can indicate the gender of the embryo with an accuracy of over 60%. The one or more metabolites can be identified using nuclear magnetic resonance.

Additional features and advantages are described herein, and will be apparent from the following Detailed Description, Drawings and the claims.

BRIEF DESCRIPTION OF THE DRAWINGS

The features, objects and advantages other than those set forth above will become more readily apparent when consideration is given to the detailed description below. Such detailed description makes reference to the following drawings, wherein:

FIG. 5A is a graph showing isoleucine modulation during the embryo development. FIG. 5B is a graph showing histidine modulation during the embryo development. The control is the value of the amino acids (histidine and isoleucine) in the medium before embryo incubation.

FIG. 6A is a graph showing valine modulation during the embryo development. FIG. 6B is a graph showing pyruvate modulation during the embryo development. The control is the value of the metabolites (valine and pyruvate) in the medium before embryo incubation.

Figure 1:
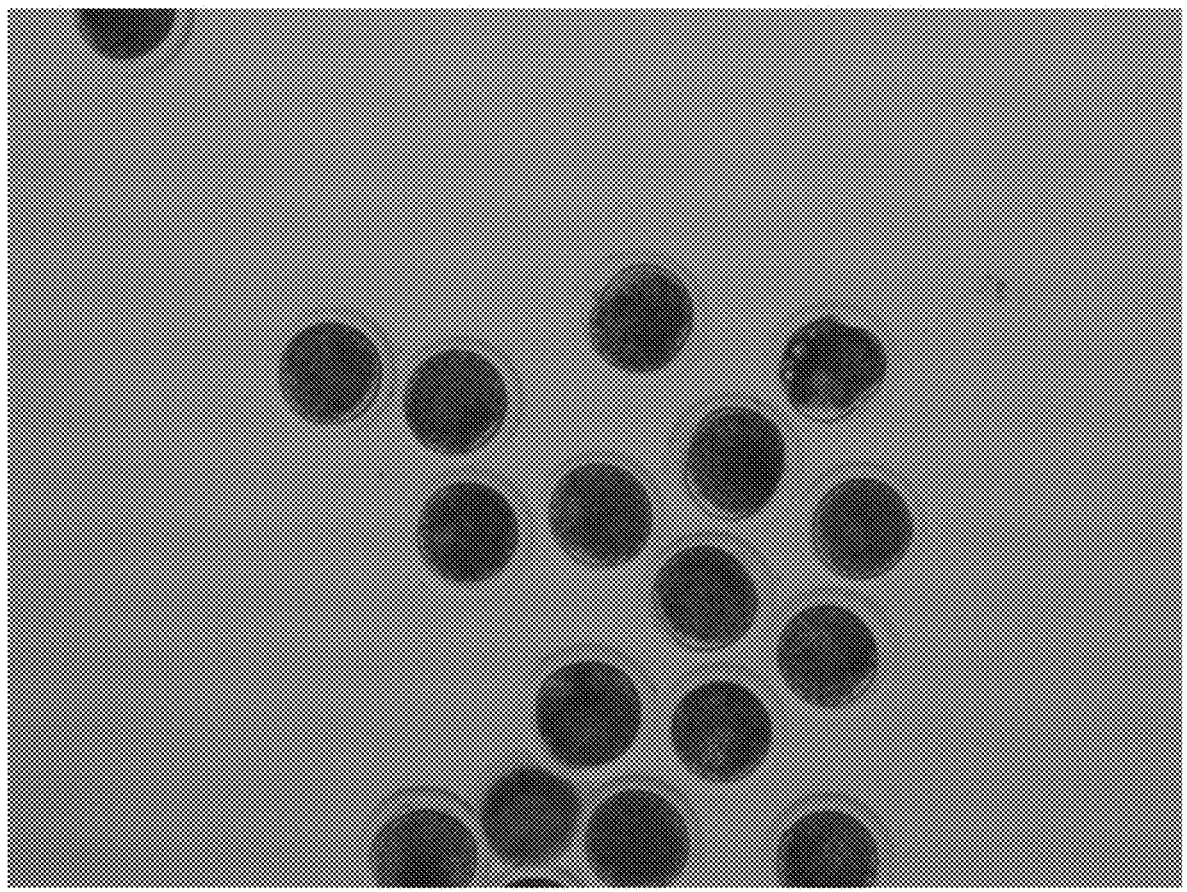
FIG. 1 shows an example of presumptive zygotes after co-incubation with sperm (day 1-0 hpi).

While the present disclosure is susceptible to various modifications and alternative forms, exemplary embodiments thereof are shown by way of example in the drawings and are herein described in detail. It should be understood, however, that the description of exemplary embodiments is not intended to limit the disclosure to the particular forms disclosed, but on the contrary, the intention is to cover all modifications, equivalents and alternatives falling within the spirit and scope of the disclosure as defined by the embodiments above and the claims below. Reference should therefore be made to the embodiments above and claims below for interpreting the scope of the disclosure.

DETAILED DESCRIPTION

The methods now will be described more fully hereinafter with reference to the accompanying drawings, in which some, but not all embodiments of the disclosure are shown. Indeed, the present disclosure may be embodied in many different forms and should not be construed as limited to the embodiments set forth herein; rather, these embodiments are provided so that this disclosure will satisfy applicable legal requirements.

Likewise, many modifications and other embodiments of the methods described herein will come to mind to one of skill in the art to which the disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the present disclosure, the preferred methods and materials are described herein. All patents, patent applications, and other scientific or technical writings referred to anywhere herein are incorporated by reference herein in their entirety.

Articles "a" and "an" are used herein to refer to one or to more than one (i.e. at least one) of the grammatical object of the article. By way of example, "an element" means at least one element and can include more than one element.

As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. The embodiments illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings.

Any single term, single element, single phrase, group of terms, group of phrases, or group of elements described herein can be each be specifically excluded from the claims.

The term "about" in association with a numerical value means that the numerical value can vary plus or minus by 5% or less of the numerical value.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the invention are described in terms of Markush groups or other grouping of alternatives, those skilled in the art will recognize that the invention is also thereby described in terms of any individual member or subgroup of members of the Markush group or other group.

The present disclosure provides non-invasive methods to determine the gender of an embryo. One aspect of the present disclosure provides a method for determining the gender of an embryo, the method comprising: (i) growing an embryo in an in vitro culture media; and (ii) identifying one or more metabolites contained in the spent culture media during early development, mid-development, and/or late development, wherein the presence of one or more metabolites indicates the gender of the embryo.

As used herein, the term "embryo" refers to an early stage of development of a multicellular diploid eukaryotic organism. An embryo can develop from a zygote, the single cell resulting from the fertilization of the female egg cell by the male sperm cell. The zygote possesses half the DNA from each of its two parents. In plants, animals, and some protists, the zygote will begin to divide by mitosis to produce a multicellular organism. The result of this process is an embryo.

In vitro production (IVP) is a type of assisted reproductive technology that involves three main sequential steps: oocyte aspiration and in vitro maturation (IVM); in vitro fertilization (IVF); and in vitro culture (IVC) of early pre-implantation embryos.

The IVM step refers to oocyte recovery from a donor by follicular aspiration, followed by in vitro maturation of oocytes. IVM media to support development of oocytes can include many components, such as hormones, trace nutrients, and growth factors such as epidermal growth factor (EGF). Examples of bovine IVM media include, but are not limited to tissue culture medium 199 (TCM199) supplemented with gonadotropin hormones and fetal calf serum (FCS).

After the maturation of oocytes in IVM (for bovine oocytes, this can be for about 22-24 hours), oocytes are subjected to fertilization in the IVF step. Examples of bovine IVF culture medium include, but are not limited to, Brackett-Oliphant medium, 4-(2-hydroxyethyl)-1-piperazineethanesulfonic acid) (HEPES)-buffered Tyrode's albumin lactate pyruvate (TALP) containing heparin, TCM199 with supplements and Tyrode's modified medium (Parrish et al. 1986, *Theriogenology*, 25(4): 591-600) without glucose and bovine serum albumin (BSA), supplemented with heparin, penicillamine, hypotaurine, epinephrine, and bovine serum (BS).

For the in vitro culture the IVC media can be synthetic fluid compositions that mimic the composition of the oviduct fluid or uterine fluids to closely approximate the natural environment of the developing embryo. They can be composed of basic salt solutions with the addition of other components, such as carbohydrates (pyruvate, lactate, and glucose), amino acids, and regulatory elements, such as hormones, growth factors and cytokines, which together comprise energy sources for the developing embryo. Examples of bovine IVC media include, but are not limited to, CR1aa, and synthetic oviduct fluid (SOF) medium (Tervit et al. 1972, *Journal of Reproduction and Fertility*, 30(3): 493-497), with essential amino acids, non-essential amino acids, and BS.

IVC media can be a single step media or a sequential media. The difference between the two types is that single step media is not changed between fertilization check and embryo transfer, or cryopreservation, while sequential media is changed out.

It will be appreciated that a variety of different IVM, IVF, and IVC media can be used with the methods of the present disclosure, and the IVM, IVF, and IVC media can vary depending on the embryo species.

Embryos can be cultured in a variety of systems. Embryos can be cultured singly or in small groups. Examples of culture systems include, but are not limited to, the well of the well (WOW) culture system, polyester mesh (PM), microfluidic channels (U.S. Pat. No. 9,157,550; Beebe, D. et al. 2002, *Theriogenology* 57:125-136; Raty, S. et al. 2004, *Lab on a Chip*, 4:186-190), and microdrops or macrodrops under paraffin oil.

Embryo transfer refers to a step in the process of assisted reproduction in which embryos are placed into the uterus of a female to establish a pregnancy. An embryo can be implanted in the same or another female's uterus, with the intention of establishing a successful pregnancy. An embryo can be implanted into a uterus of an animal that was not the egg donor, resulting in genetically unrelated offspring to animal that carried the pregnancy. This technique is a non-naturally occurring reproduction method that can be used in animals (including humans). Embryo transfer can be used to disseminate desirable genes from superior female animals from various species (e.g., horses, cattle, sheep, goats, and pigs). Advantages of embryo transfer include, but are not limited to, an increased number of offspring per female, a reduction in the generation interval for animals with desirable traits, a rapid expansion of an animal population, improved management of efficiency and facility flexibility, elimination of recessive genes, and genotype selection (e.g., animals that are free from disease and have desirable characteristics).

The types of animals that can undergo embryo transfer include, but are not limited to, invertebrates (e.g., worms, mollusks, or octopuses), fish (e.g., tuna, salmon, sharks, rays, or skates), amphibians (e.g., frogs, toads, or salamanders), reptiles (e.g., crocodiles, alligators, turtles, tortoises, snakes, or lizards), birds (e.g., doves, pigeons, flamingos, ostriches, or penguins), and mammals (e.g., humans, monkeys, rats, cats, dogs, seals, cows, horses, pigs, sheep, or goats). An embryo used in the methods of the present disclosure can be from any animal that is capable of undergoing an embryo transfer (e.g., a human, cow, pig, horse, sheep, goat, dog, cat, mouse, rat, rabbit, or chicken). In some embodiments, the embryo used in the methods of the present disclosure can be a human embryo, bovine embryo, a porcine embryo, an equine embryo, an ovine embryo, a hircine embryo, a canine embryo, a feline embryo, a murine embryo, a rabbit embryo, a chicken embryo, a carnivore embryo, a herbivore embryo, a rodent embryo, a bird embryo, a mammalian embryo. In some embodiments, the embryo used in the methods of the present disclosure can be a bovine embryo.

As used herein, the term "non-invasive" refers to the ability to assess the gender of an embryo without having to disrupt the embryo or any cells of the embryo. For example, analyzing the spent culture media of the embryonic cell culture using spectroscopy (e.g., 1H NMR spectroscopy) can be a non-invasive way to assess the gender of an embryo.

The term "spent media" as used herein refers any media that is used to culture or grow one or more oocytes or embryos. Spent media can be obtained from any point in time or step of the methodologies described herein and can be derived from either single step media culturing procedures or sequential media culturing procedures. Spent media can be harvested from oocyte or embryo cultures at any period of time (e.g., about 5, 10, 60, 120 or more minutes, about 3, 5, 10, 12, 24, 36, 48, 68 or more hours, about 3, 4, 5, 6, 7, 8, 9, 10, 11, 12, or more days or any range from about 5 minutes to about 12 days). In an embodiment discarded media that is changed out with sequential media is spent culture media. Spent media can be cell culture media that has been depleted of one or more nutrient(s), has been dehydrated, or has accumulated metabolic or other by-products that could be harmful or toxic to the cells. The spent media can be collected and stored for later analysis without impacting the viability of the oocyte or embryo.

The contents of the spent culture media can be analyzed during different stages of the embryonic development: (1) before the embryonic genome is established (early development) (2) intermediate phase when there are a high cleavage phase (mid-development); and (3) formation of blastocysts (late development). Early development can be about 1 day to about 3 days after a zygote is formed or about 24 hours to about 72 hours after a zygote is formed. For example, early development can be about 1 day, 2 days or 3 days after a zygote is formed. Early development can also be about 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, 61 hours, 62 hours, 63 hours, 64 hours, 65 hours, 66 hours, 67 hours, 68 hours, 69 hours, 70 hours, 71 hours, or 72 hours after a zygote is formed (or any range between about 24 hours and 72 hours).

Mid-development can be about 3 days to about 5 days after a zygote is formed or about 72 hours to about 120 hours after a zygote is formed. For example, mid-development can be about 3 days, 4 days or 5 days after a zygote is formed. Early development can also be about 72 hours, 73 hours, 74 hours, 75 hours, 76 hours, 77 hours, 78 hours, 79 hours, 80 hours, 81 hours, 82 hours, 83 hours, 84 hours, 85 hours, 86 hours, 87 hours, 88 hours, 89 hours, 90 hours, 91 hours, 92 hours, 93 hours, 94 hours, 95 hours, 96 hours, 97 hours, 98 hours, 99 hours, 100 hours, 101 hours, 102 hours, 103 hours, 104 hours, 105 hours, 106 hours, 107 hours, 108 hours, 109 hours, 110 hours, 111 hours, 112 hours, 113 hours, 114 hours, 115 hours, 116 hours, 117 hours, 118 hours, 119 hours, or 120 hours after a zygote is formed (or any range between about 72 hours and 120 hours).

Late development is about 5 days to about 7 days after a zygote is formed or about 120 hours to about 168 hours after a zygote is formed. For example, late development can be about 5 days, about 6 days, or about 7 days after a zygote is formed. Late development can also be about 120 hours, 121 hours, 122 hours, 123 hours, 124 hours, 125 hours, 126 hours, 127 hours, 128 hours, 129 hours, 130 hours, 131 hours, 132 hours, 133 hours, 134 hours, 135 hours, 136 hours, 137 hours, 138 hours, 139 hours, 140 hours, 141 hours, 142 hours, 143 hours, 144 hours, 145 hours, 146 hours, 147 hours, 148 hours, 149 hours, 150 hours, 151 hours, 152 hours, 153 hours, 154 hours, 155 hours, 156 hours, 157 hours, 158 hours, 159 hours, 160 hours, 161 hours, 162 hours, 163 hours, 164 hours, 165 hours, 166 hours, 167 hours, or 168 hours after a zygote is formed (or any range between about 120 hours and 168 hours).

It will be appreciated that the timeframe for early development, mid-development, and late-development may vary depending on the embryo species.

The methods of the present disclosure utilize non-invasive metabolomic analysis of embryos. Metabolomic analysis is an approach used in biological systems, defined as "a non-targeted quantitative analysis of tissue and biofluids for low molecular mass organic endogenous metabolites" (Nadal-Desbarats et al. 2012 *MAGMA,* 26(2):193-202). Metabolic profiles and their changes over time due to physiological and/or pathophysiological stimuli such as disease, toxicity, nutritional and other effects provide important information that assists with the understanding of biological regulation and physio-pathological mechanisms (Lindon et al. 2003, *Toxicology and Applied Pharmacology,* 187(3): 137-146). Changes in steady-state concentrations and transient changes in intracellular metabolites resulting from processes such as cell signaling can be readily investigated using metabolomic techniques such as high-resolution nuclear magnetic resonance (1H NMR) spectroscopy.

1H NMR spectroscopy can be a powerful technique for metabolomic analysis of biological fluids. NMR spectroscopy is capable of studying intact tissues and fluids, producing a comprehensive profile of metabolites (Kumar et al. 2014, *NMR in Biomedicine,* 27(1):80-89). An important aspect of NMR spectroscopy is that the fundamental physicochemical mechanisms are completely different from other common analytical techniques and provide a different scientific perspective (Pauli et al. 2005, *Journal of Natural Products*, 68(1):133-149). Specifically, NMR spectroscopy is different from chromatographic procedures (such as HPLC), which, in combination with mass spectrometry, are currently the most commonly used methods for identification and quantification of molecular species in a sample. Because chromatography requires a thorough knowledge of the sample's chemical properties, it is limited to the specific chemical's dynamic range and separation methods (Pauli et al. 2005, *Journal of Natural Products*, 68(1):133-149), whereas NMR is limited only by magnetic field strength and does not require sample separation (Seli et al. 2008, *Fertility and Sterility*, 90(6):2183-89). A multitude of compounds can be targeted using 1H NMR spectroscopy (Graca et al. 2009, *Journal of Proteome Res*, 8(8):4144-4150; Wishart et al. 2008, *Journal of Chromatography B*, 871(2):164-173). 1H NMR spectroscopy can be used as a non-invasive technique to identify one or more metabolites contained in the spent media that can be used to assess, determine, indicate, or predict the gender of an embryo.

On the other hand, if a sample's chemical properties can be estimated (e.g., the presence of valine during early development or the presence of pyruvate during late development), chromatography techniques can also be used as a non-invasive way to assess, determine, indicate, or predict the gender of an embryo. Types of chromatography techniques include, but are not limited to, column chromatography, paper chromatography, thin layer chromatography, gas chromatography, high performance liquid chromatography (HPLC), fast protein liquid chromatography, supercritical fluid chromatography, affinity chromatography, reversed phase chromatography, two dimensional chromatography, pyrolysis gas chromatography, and counter current chromatography.

In some embodiments, the gender of the embryo is determined before the embryo is transferred into an animal.

An embodiment provides a method for determining the gender of an embryo. The method comprises growing an embryo in an in vitro culture media. Spent media can be collected. One or more metabolites can be identified in the spent media and quantified in the spent culture media of the embryo during early development, mid-development, late development, or a combination thereof. The presence of one or more metabolites at a concentration that varies (either higher or lower) from a base line concentration can indicate the gender of the embryo. The one or more metabolites can be, for example, an amino acid, a sugar, or a nucleotide. Examples include formate, lactate, myo-inositol, citrate, pyruvate, acetate, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine or a combination thereof. The concentration of the one or more metabolites can vary by 0.5, 1, 2, 3, 4, 5, 10, 20, 30, 40% or more from baseline (either greater or lesser concentration).

In an embodiment the presence of valine during early development in a concentration above a base line indicates that the embryo will more likely be male than female.

In an embodiment, the presence of valine during early development in a concentration below or about a base line indicates that the embryo will more likely be female than male.

In an embodiment the presence of pyruvate during late development in a concentration at about or below a base line indicates that the embryo will more likely be female than male.

In an embodiment the presence of pyruvate during late development in a concentration above a base line indicates that the embryo will more likely be male than female.

The terms "determine," "predict," or "indicate" when used in the context of "determining/predicting/indicating the gender of an embryo" refers to being able to use one or more metabolites to say that the gender of the embryo will either be male or female with greater than about 50% (e.g., about 51%, 52%, 53%, 54%, 55%, 56%, 57%, 58%, 59%, 60%, 61%, 62%, 63%, 64%, 65%, 66%, 67%, 68%, 70%, 75%, 80% or more) accuracy, greater than about 40% sensitivity (e.g., 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70% or more), or greater than about 60% specificity (e.g., 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85% or more). In some embodiments, the presence of the one or more metabolites indicates the gender of the embryo with an accuracy of over 60%.

For example, the presence of valine in the spent media of an embryonic cell culture during early development in a concentration above the baseline of that in the embryo or of that in the normal concentration in the media it is cultured in can indicate that the embryo will be male with an accuracy of about 66.7%, a sensitivity of about 60%, and a specificity of about 73.3%. Alternatively, the presence of valine during early development in a concentration below or about the base line can indicate that the embryo will more likely be female than male.

As another example, the presence of pyruvate during late development in a concentration above the base line can indicate that the embryo will be male with an accuracy of about 64.0%, a sensitivity of about 40%, and a specificity of about 80.0%. Alternatively, the presence of pyruvate during late development in a concentration at about or below the baseline can indicate that the embryo will more likely be female than male.

The term "baseline" as used herein refers to the level of one or more metabolites in the media of an embryo as determined on day 1 of embryonic development. Day 1 of embryonic development is considered as the day a zygote divides to form an embryo. In an embodiment, a baseline is established 1, 2, 5, 10, 15, 20, or 24 hours after formation of an embryo. A baseline is compared to a level of one or more metabolites in the spent media of the embryonic cell at a later time. A later time can be for example, about 5, 10, 60, 120 or more minutes, about 3, 5, 10, 12, 24, 36, 48, 68 or more hours, about 3, 4, 5, 6, 7, 8, 9, 10, 11, 12, or more days or any range from about 5 minutes to about 12 days).

The methods of the present disclosure can be used to identify one or more metabolites in the spent culture media.

Metabolites can be organic compounds that are starting materials/intermediates in metabolism pathways in the body of animals or humans. Metabolites can be produced when cells break down food, nutrients, drugs, or chemicals, or cells or tissue. Metabolites can include low molecular weight organic compounds within a mass range of about 50 Daltons to 1500 Daltons. Metabolites include, but are not limited to, amino acids, sugars, nucleotides, lipids, or carbohydrates.

Amino acid metabolites can be organic compounds containing amine ($-NH_2$) and carboxyl ($-COOH$) functional groups, along with a side chain (R group) specific to each amino acid. There are about 500 naturally occurring amino acids are known (with only 20 appearing in the genetic code) and can be classified in many ways. Amino acids can be classified according to the core structural functional groups' locations as alpha- (α-), beta- (β-), gamma- (γ-) or delta- (δ) amino acids; other categories relate to polarity, pH level, and side chain group type (aliphatic, acyclic, aromatic, containing hydroxyl or sulfur, etc.). There are essential and non-essential amino acids. Essential amino acids cannot be made by the embryo and come from outside sources (e.g., food or cell culture media). Essential amino acids include, but are not limited to, histidine, isoleucine, leucine, lysine, methionine, phenylalanine, threonine, tryptophan, and valine. Non-essential amino acids are made by the embryo, and can include, but are not limited to, alanine, arginine, asparagine, aspartic acid, cysteine, glutamic acid, glutamine, glycine, proline, serine, and tyrosine.

Amino acid metabolites as referred to herein include, but are not limited to, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and/or valine Sugar metabolites include, but are not limited to, glucose, lactose, sucrose, fructose, sorbitol, ribose, deoxyribose, formate, lactate, myo-inositol, D-chiro-inositol, citrate, pyruvate, acetate.

In an embodiment, a metabolite can be present in spent culture media at about 1, 2, 3, 4, 5, 10, 15, 20, 25% or more than a baseline measurement of that metabolite. In an embodiment, a metabolite can be present in spent culture media at about 1, 2, 3, 4, 5, 10, 15, 20, 25% or less than a baseline measurement of that metabolite. In an embodiment, a difference in the level or amount of a metabolite in spent culture media as compared to a baseline level or amount of a metabolite in culture media indicates a greater or lesser specificity, sensitivity, or probability that an embryo is a male or female embryo.

The metabolites that can be identified through the methods described herein can occur in an in vitro environment in concentrations that are not found in a natural setting (e.g., in an embryo grown in an in vivo environment). That is, the metabolites of an in vitro cultured embryo are different from those occurring in a natural, in vivo environment.

Another embodiment provides a method of determining a marker for gender evaluation of an embryo, the method comprising: (i) growing an embryo in an in vitro culture media; (ii) identifying one or more metabolites contained in the spent culture media during early development, mid-development, and late development using, for example, nuclear magnetic resonance or another suitable methods; (iii) comparing the concentrations of the one or more metabolites contained in the spent culture media during early development, mid-development, and late development to identify trends in the depletion or accumulation of one or more metabolites during early development, mid-development, or late development; and (iv) correlating the depletion or accumulation of one or more metabolites during early development, mid-development, or late development to the actual gender of the embryo.

Another embodiment provides a tool for diagnosis of sex-linked diseases in embryos of humans. Certain genetic diseases are associated with one sex. Patients that are carriers for such diseases may not want a child with that sex if it has a chance to carry a sex-linked disease. The current method for screening requires micro surgery of the embryo, which decreases the viability and pregnancy rate of that embryo. The methodology described herein can allow for a non-invasive determination of the embryo sex, which would allow a decision whether to transfer that embryo or not. Examples of sex-linked diseases include, for example, hemophilia, Duchenne muscular dystrophy, fragile-X syndrome, some high blood pressure, congenital night blindness, and G6PD deficiency.

Therefore, an embodiment provides a method of avoiding an embryo having a chance of carrying a sex-linked disease comprising determining the gender of an embryo by growing an embryo in an in vitro culture media and identifying one or more metabolites contained in the spent culture media during early development, mid-development, late development, or a combination thereof wherein the presence of one or more metabolites indicates the gender of the embryo. In an embodiment, the presence of one or more metabolites during development at a concentration above or below a base line as described herein indicates the gender of the embryo. A male or female embryo at risk of carrying a sex-linked disease can then be avoided for implantation and further development. A male or female embryo not at risk of carrying a sex-linked disease can then be selected for implantation and further development.

The term "depletion" as used herein refers to a reduction in the number, quantity, or concentration of one or more metabolites.

The term "accumulation" as used herein refers to an increase in the number, quantity, or concentration of one or more metabolites.

The term "prediction variable" as used herein refers to one or more metabolites (e.g., valine or pyruvate) that are capable of predicting the gender of an embryo that is grown in an in vitro environment.

Methods of evaluating and correlating changes in one or more metabolites over time in the spent culture media of an embryo can be achieved using statistical analysis techniques known in the art and described in the examples below.

The practice of the present disclosure employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Furthermore, the terminology used herein is for the purpose of exemplifying particular embodiments only and is not intended to limit the scope of the disclosure as disclosed herein. Any method and material similar or equivalent to those described herein can be used in the practice of the disclosure as disclosed herein and only exemplary methods, devices, and materials are described herein.

The disclosure now will be exemplified for the benefit of the artisan by the following non-limiting examples that depict some of the embodiments by and in which the disclosure can be practiced.

EXAMPLES

Materials and Methods
Reagents and Media
Unless otherwise stated, all reagents were purchased from Sigma-Aldrich (USA). The IVF medium was Tyrode's modified medium (Parrish et al. 1986, *Theriogenology*, 25(4): 591-600) without glucose and bovine serum albumin (BSA), supplemented with 95.6 USP/mL heparin, 30 µM penicillamine, 15 µM hypotaurine, 1 µM epinephrine, and 1% bovine serum (BS). The in vitro culture (IVC) medium consisted of synthetic oviduct fluid (SOF) medium (Tervit et al. 1972, *Journal of Reproduction and Fertility*, 30(3):493-497), with 30 µL/mL essential amino acids, 10 µL/mL non-essential amino acids, and 5% BS.

In Vitro Embryo Production

Matured oocytes were purchased from DeSoto Biosciences (Seymour, Tenn., USA). In vitro matured COCs were washed and transferred, 20-30 per well, into 300 µL of IVF medium covered with mineral oil. For each replicate, two straws of frozen semen (from a bull previously tested for IVF, Interglobe Genetics, Pontiac, Ill.) were thawed at 37° C. for 40 s. The sample was then processed via Percoll discontinuous gradient (45-80%) (Sattar et al. 2011, *Reproduction in Domestic Animals*, 46(6):1090-1097). After processing, pellets were diluted with IVF medium and added to the fertilization wells at the concentration of 1×106 sperm/mL. Gametes were co-incubated for 18-20 h at 39° C., in 5% $CO_2$ in air, after which presumptive zygotes were vortexed for 2 min to remove cumulus cells in HEPESTCM with 5% BS, washed twice in the same medium. Presumptive zygotes were placed in SOF, where they were incubated in a humidified mixture of 5% CO2, 6% O2, and 89% N2, at 39° C. (day 1). The zygotes were place in 50 µL drops or in a multiwell plate with 400 µL, in both vessels the medium was covered with mineral oil.

Embryo Culture: Days 1-3

After co-incubation (day 1-0 hpi) (FIG. 1) the presumptive zygotes were placed in individual drops of 50 µL of SOF, where they were incubated in a humidified mixture of 5% CO2, 6% O2, and 89% N2 at 39° C. After 48 h of culture (day 3-48 hpi), the zygotes were placed into well-of the-well (WOW) culture (Vajta et al. 2008, *Reproductive Biomedicine Online*, 17(1):73-81), to follow the individual zygotes in a group culture system. After culture, the media drops were collected and stored in 1.5 mL microfuge tubes and frozen at −80 C until NMR analysis.

Embryo Culture: Days 3-5

Figure 2:
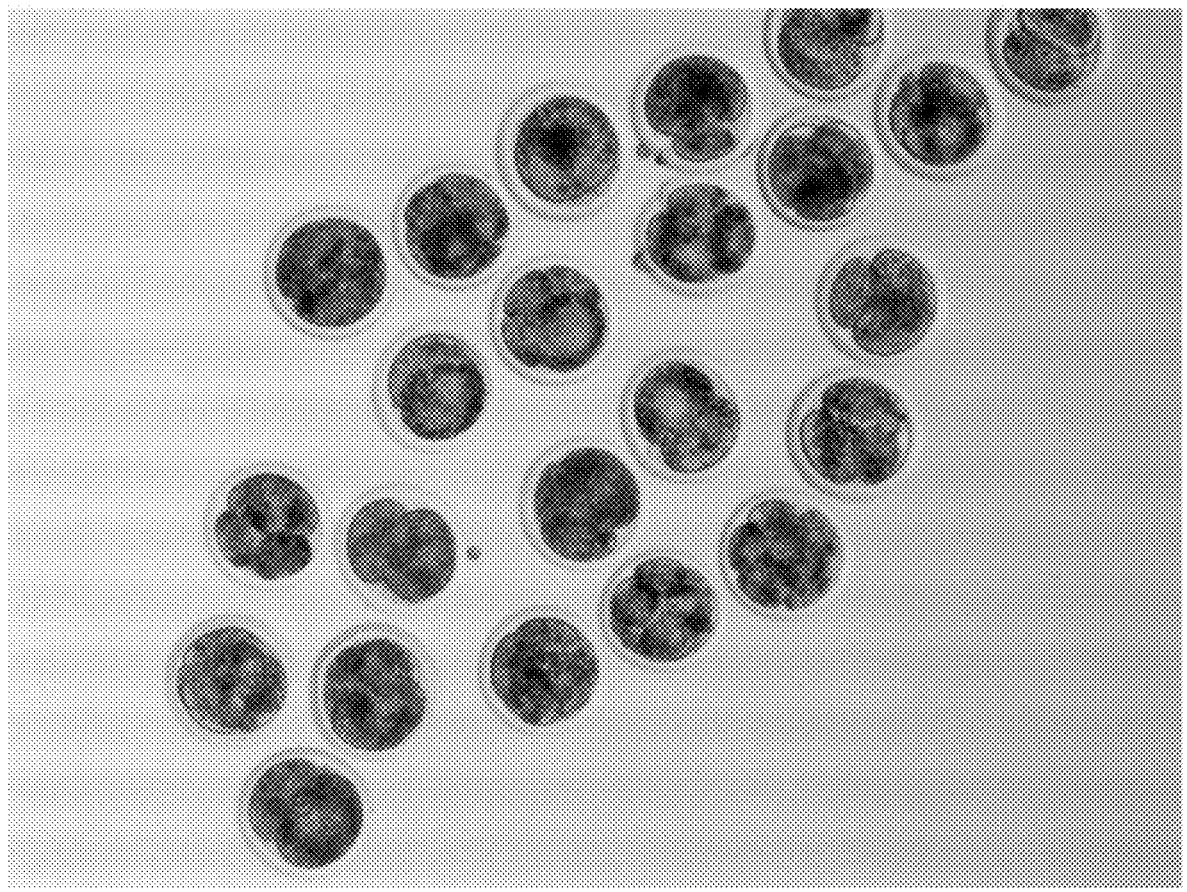
FIG. 2 shows an example of zygotes after 48 h (day 3) of culture.

After co-incubation (day 1-0 hpi), the presumptive zygotes were put in multi-well plates for 48 h of culture (day 3) (FIG. 2), followed by placement in individual drops of 50 µL of SOF for 48 h (day 5-95 hpi), and finally placed into WOW culture. After culture, the media drops were collected and stored as above described until NMR analysis.

Embryo Culture: Days 5-7

Figure 3:
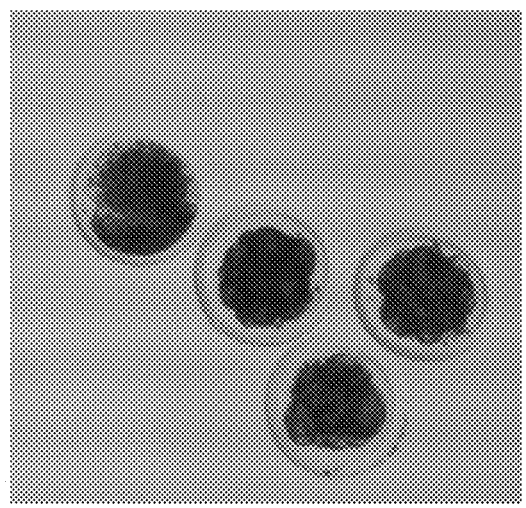
FIG. 3 shows an example of zygotes after 96 h (day 5) of culture.

After co-incubation (day 1-0 hpi), the zygotes were put in the multi-well plate for 96 h (day 5) (FIG. 3). After that, they were placed in individual drops of 50 µL of SOF for an additional 48 h of culture (day 7). At the end of the culture, the embryos were evaluated and scored. After culture, the media drops were collected and stored as above described until NMR analysis. The embryos were scored for quality on the basis of morphological criteria, and only Grade 1 and 2 blastocysts (Bl) were considered in the evaluation of the final embryo rate (Robertson and Nelson 1998). Embryos were put into 10 µL of PBS, and stored individually at −80° C. until the evaluation of the embryo's sex.

Embryo Sexing

20 µL of lysis buffer containing 15 mM Tris-HCl pH 8.9, 50 mM KCl, 2.5 mM $MgCl_2$, 0.1% Triton X-100, and 150 µg/mL proteinase K was added to each tube. The tubes were incubated at 55° C. for 1 h, then proteinase K was inactivated by incubation at 90° C. for 10 min. For each round of PCR, purified male DNA prepared from blood of adult cattle were used as positive controls (Wizard Genomic DNA Purification Kit-Promega cat. A1125). Amplifications were performed by adding 12.5 µL of a PCR mix (JumpStart™ Taq ReadyMix™), two pairs of primers (1 µL for each pair), 1 µL of template DNA, and 10.5 µL of $H_2O$ to each PCR tube for a total volume of 25 µL per tube. Each pair of primers was amplified individually. The first pair is specific to a sex-determining region of the bovine Y chromosome (SRY) (Daneau et al. 1995, *Biology of Reproduction*, 52(3): 591-599), while the second pair of primers is specific to an autosomal gene (tRep-137) (Alomar et al. 2008, *Animal Reproduction Science*, 107(1-2):48-61; Sattar et al. 2011, *Reproduction in Domestic Animals*, 46(6): 1090-1097) (Table 1).

TABLE 1

Sequences and quantities of primers used for embryo sexing, sizes of the obtained amplicons

| Gene | Primer sequence | Quantity (nmol) | PCR product (bp) |
|---|---|---|---|
| bSRY A | ACAGTCATAGCGCAAATGATCAGTG (SEQ ID NO: 1) | 250 | 342 |
| bSRY 1 | GGGTTGCATAGTATTGAAGAGTCTGC (SEQ ID NO: 2) | 250 | |
| btRep-137 C1 | TATTTTCGGAACGCGGGAGAGAAGAG-3 (SEQ ID NO: 3) | 220 | 450 |
| btRep-137 C2 | TATTTTTGATTCCCTCCGTGCGGCGC TTA-3 (SEQ ID NO: 4) | 220 | |

Figure 4:
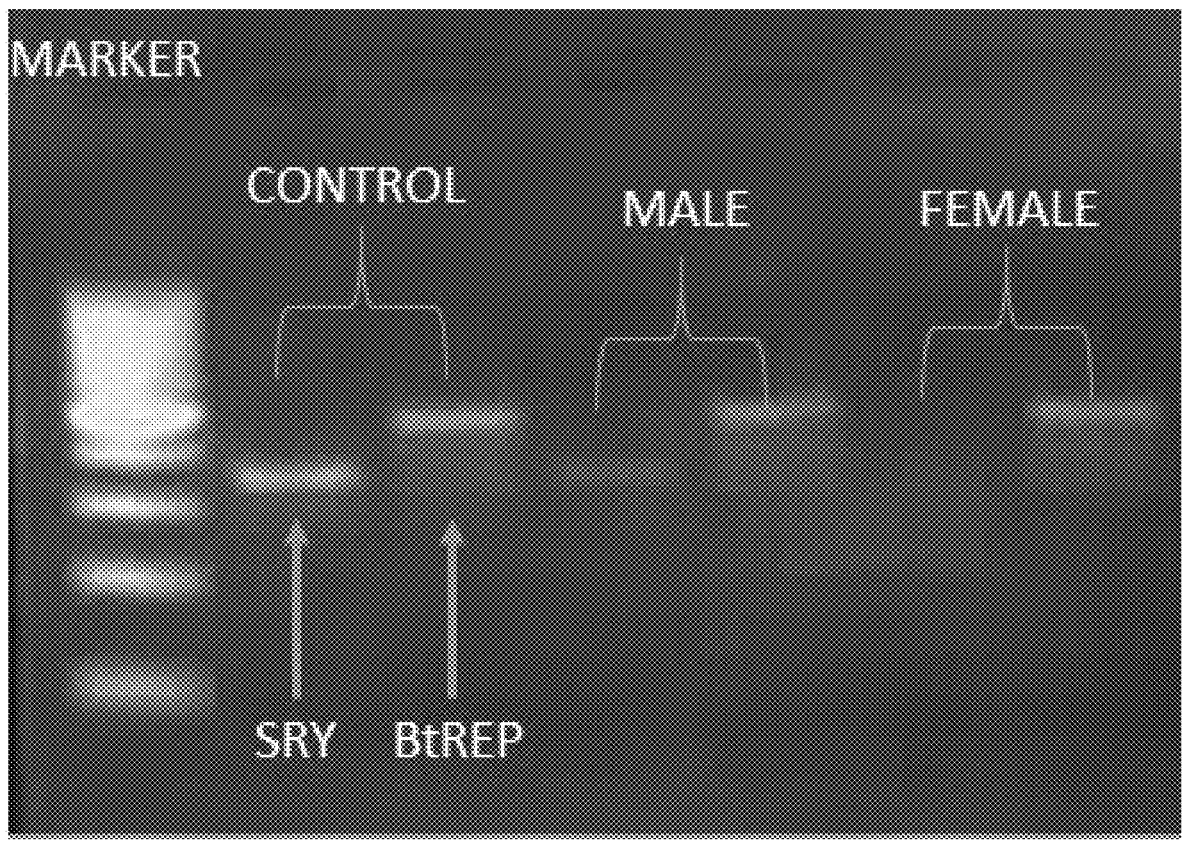
FIG. 4 is a gel showing the separated PCR products after amplification of male and female specific DNA sequences from individual IVF embryos.

All samples were denatured at 95° C. for 15 min, followed by 39 cycles consisting of denaturation at 96° C. for 30 s, annealing at 52° C. for 30 s, and extension at 72° C. for 45 s. After the last cycle, all samples were incubated for a further 5 min to assure complete extension. PCR products were analyzed using a 2% agarose gel with 0.1 µg/mL of ethidium bromide in the gel. The resulting bands migrated by electrophoresis and the products were observed with UV transillumination. Each template was allocated in a single well so that each embryo corresponds to two adjacent wells. Therefore, the embryo was assessed as male when both bands were visible in the corresponding spots, and as female when in two adjacent wells only one band was visible (FIG. 4).

1H NMR Spectroscopy

Samples of media (40 µL) were thawed at room temperature and added to 660 µL of a stock solution prepared by dissolving 5.0 mg of sodium 3-(trimethylsilyl)-2,2',3,3'-tetradeuteropropionate (TSP) in 50 mL of deuterium oxide. The TSP acted both as a chemical shift reference and as an internal standard for the purposes of quantitation. The resulting diluted samples were transferred to a 5-mm NMR tube. Samples were analyzed on a 750-MHz Agilent VNS750NB spectrometer (Agilent Technologies, Santa Clara, Calif.) equipped with a 5 mm Varian HCN PFG X, Y, Z-probe at 23° C. Shimming of the sample was performed manually on the residual water signal. 1H NMR spectra were recorded with a 90° radio frequency pulse (pulse width=6.3 µs, transmitter power=63 dB). Sixty four scans were acquired in 16 K data points with a spectral width of 7100 Hz and a relaxation delay of 10 s. The residual water signal at 4.8 ppm was suppressed using the "presat" pulse sequence (saturation power=9 dB, presaturation delay=2 s). Spectra were processed with MestReNova software, version 6.0 (Mestrelab Research, Santiago de Compostela, Spain). Prior to Fourier transformation, the FIDs (Free Induction Decay) were zero-filled to 32 K. All spectra were manually phased and corrected for baseline distortion. Peak integrals were obtained using the MestReNova software integral function and normalized with respect to the number of protons comprising the signal. The concentration of the analytes was calculated by determining the ratio of the normalized integrals of the corresponding 1H NMR signals to the TSP signal integral (0 ppm, singlet, Si(CH3)3). Signal assignments were made on the basis of previously published data (MacIntyre et al. 2011, *PLoS ONE*, 6(2):e16732; Nadal-Desbarats et al. 2012, *MAGMA*, 26(2):193-202; Wallace et al. 2014, *Systems Biology in Reproductive Medicine*, 60(1): 58-63).

Statistical Analysis

The changes in each amino acid and sugar were evaluated in the early (1-3), middle (day 3-5), and later (day 5-7) periods using mixed models with repeated measures in SAS. Data with P-values lower than 0.05 were considered statistically significant. To characterize the variation of the media content with a few variables, reduce the redundancy among variables, and detect linear relationships, a principal component analysis (PCA) was undertaken in SAS (SAS Institute, Cary, N.C.). The first two principal components were plotted by period. The degree by which variables measured during the three periods could be predictive of the gender of the embryo was determined by logistic regression. The binary outcomes were defined as 1 for female or as 0 for a male. Before the analysis and in order to select the subset of metabolites to include in the final analysis, a stepwise selection was performed with the six sugars and nine amino acids metabolites as independent variables. Only variables with a P-value<0.05 were considered and retained in the final model. The results were presented as the estimated effect, standard error of the estimated effect, P-value, and marginal means associated with the effect.

Example 1: Determining Markers for Gender Evaluation of an Embryo

The aim of this study was to evaluate embryo metabolism during three important periods of in vitro development: early development, before X inactivation (from day 1 until day 3), the middle of culture, before the differentiation into ICM and trophectoderm (day 3 until day 5), and later development, during the blastocyst formation (day 5 until day 7). Six sugars (pyruvate, citrate, formate, lactate, myo-inositol, acetate) and nine amino acids (alanine, leucine, isoleucine, valine, histidine, tyrosine, lysine, methionine, and phenylalanine) were evaluated. Using these molecules, a pattern of metabolic activity during embryo development was discovered.

To determine markers for evaluating the gender of embryos, 20 spent media drops per gender per time point (1-3 days, 3-5 days, and 5-7 days) for a total of 40 samples (20 male and 20 female) were analyzed. The spent medium for each time point was analyzed only after embryo evaluation. Four samples for each blastocyst stage were collected. The embryos were randomly collected from at least three replicates. Therefore, for each group, four tight morulas, four early blastocysts, four blastocysts, four expanded blastocysts and four hatched blastocysts were evaluated. A total of 120 embryos were evaluated. The embryo rate was variable from 7 to 35%; the lowest rates resulted from presumptive zygotes, which had been plated in single drops in the first days of development. A total of 1000 oocytes were fertilized in five replicates.

The results suggest that differences in metabolites came from the differences in requirements across time rather than gender (Table 2 and Table 3)

TABLE 2

Impact (P-value) of the period of culture [early (days 1-3), middle (days 3-5), and late (days 5-7)], the gender of the embryo, and the interaction between the two of them on the in vitro metabolic activity of the sugars and amino acid evaluated in the univariate analysis.

|  | Period | Gender | Day × gender |
|---|---|---|---|
| Formate | 0.0241 | 0.2058 | 0.0867 |
| Phenylalanine | <0.0001 | 0.6037 | 0.5513 |
| Histidine | <0.0001 | 0.2119 | 0.0013 |
| Tyrosine | <0.0001 | 0.4158 | 0.0621 |
| Lactate | <0.0001 | 0.3285 | 0.7136 |
| Myo-inositol | 0.0004 | 0.1265 | 0.1228 |
| Lysine | <0.0001 | 0.8552 | 0.3273 |
| Citrate | <0.0001 | 0.1671 | 0.1481 |
| Pyruvate | 0.0030 | 0.0168 | 0.0003 |
| Methionine | <0.0001 | 0.1183 | 0.4455 |
| Acetate | 0.1011 | 0.8675 | 0.8126 |
| Leucine | <0.0001 | 0.2325 | 0.6210 |
| Isoleucine | 0.3693 | <0.0001 | 0.0008 |
| Alanine | 0.0003 | 0.1951 | 0.7813 |
| Valine | 0.9531 | <0.0001 | 0.0004 |

TABLE 3

Mean and standard error by effects for each metabolite and interaction

| Effect | DAY | SEX | Estimate | Standard Error |
|---|---|---|---|---|
| Formate | | | | |
| DAY | 1_3 | | 0.1483 | 0.03406 |
| DAY | 3_5 | | 0.2820 | 0.03466 |
| DAY | 5_7 | | 0.1940 | 0.03406 |
| SEX | | F | 0.2333 | 0.02813 |
| SEX | | M | 0.1829 | 0.02781 |
| DAY*SEX | 1_3 | F | 0.1480 | 0.04816 |
| DAY*SEX | 1_3 | M | 0.1487 | 0.04816 |
| DAY*SEX | 3_5 | F | 0.3700 | 0.04985 |
| DAY*SEX | 3_5 | M | 0.1940 | 0.04816 |
| DAY*SEX | 5_7 | F | 0.1820 | 0.04816 |
| DAY*SEX | 5_7 | M | 0.2060 | 0.04816 |
| Phenylalanine | | | | |
| DAY | 1_3 | | 0.2607 | 0.005849 |
| DAY | 3_5 | | 0.1040 | 0.005952 |
| DAY | 5_7 | | 0.1007 | 0.005849 |
| SEX | | F | 0.1533 | 0.004832 |
| SEX | | M | 0.1569 | 0.004775 |
| DAY*SEX | 1_3 | F | 0.2640 | 0.008271 |
| DAY*SEX | 1_3 | M | 0.2573 | 0.008271 |
| DAY*SEX | 3_5 | F | 0.1007 | 0.008561 |
| DAY*SEX | 3_5 | M | 0.1073 | 0.008271 |
| DAY*SEX | 5_7 | F | 0.09533 | 0.008271 |
| DAY*SEX | 5_7 | M | 0.1060 | 0.008271 |
| Histidine | | | | |
| DAY | 1_3 | | 0.1927 | 0.005149 |
| DAY | 3_5 | | 0.1043 | 0.005240 |
| DAY | 5_7 | | 0.1090 | 0.005149 |
| SEX | | F | 0.1391 | 0.004254 |
| SEX | | M | 0.1316 | 0.004204 |
| DAY*SEX | 1_3 | F | 0.2100 | 0.007282 |
| DAY*SEX | 1_3 | M | 0.1753 | 0.007282 |
| DAY*SEX | 3_5 | F | 0.1086 | 0.007537 |
| DAY*SEX | 3_5 | M | 0.1000 | 0.007282 |
| DAY*SEX | 5_7 | F | 0.09867 | 0.007282 |
| DAY*SEX | 5_7 | M | 0.1193 | 0.007282 |
| Tyrosine | | | | |
| DAY | 1_3 | | 0.2150 | 0.004662 |
| DAY | 3_5 | | 0.1117 | 0.004745 |

TABLE 3-continued

Mean and standard error by effects for each metabolite and interaction

| Effect | DAY | SEX | Estimate | Standard Error |
|---|---|---|---|---|
| DAY | 5_7 | | 0.1147 | 0.004662 |
| SEX | | F | 0.1449 | 0.003852 |
| SEX | | M | 0.1493 | 0.003807 |
| DAY*SEX | 1_3 | F | 0.2200 | 0.006593 |
| DAY*SEX | 1_3 | M | 0.2100 | 0.006593 |
| DAY*SEX | 3_5 | F | 0.1107 | 0.006825 |
| DAY*SEX | 3_5 | M | 0.1127 | 0.006593 |
| DAY*SEX | 5_7 | F | 0.1040 | 0.006593 |
| DAY*SEX | 5_7 | M | 0.1253 | 0.006593 |
| Lactate | | | | |
| DAY | 1_3 | | 2.7540 | 0.06213 |
| DAY | 3_5 | | 3.1733 | 0.06323 |
| DAY | 5_7 | | 3.1243 | 0.06213 |
| SEX | | F | 2.9817 | 0.05133 |
| SEX | | M | 3.0527 | 0.05073 |
| DAY*SEX | 1_3 | F | 2.7100 | 0.08787 |
| DAY*SEX | 1_3 | M | 2.7980 | 0.08787 |
| DAY*SEX | 3_5 | F | 3.1779 | 0.09096 |
| DAY*SEX | 3_5 | M | 3.1687 | 0.08787 |
| DAY*SEX | 5_7 | F | 3.0573 | 0.08787 |
| DAY*SEX | 5_7 | M | 3.1913 | 0.08787 |
| Myo-inositol | | | | |
| DAY | 1_3 | | 2.3440 | 0.05373 |
| DAY | 3_5 | | 2.0709 | 0.05468 |
| DAY | 5_7 | | 2.0680 | 0.05373 |
| SEX | | F | 2.1128 | 0.04439 |
| SEX | | M | 2.2091 | 0.04387 |
| DAY*SEX | 1_3 | F | 2.3440 | 0.07598 |
| DAY*SEX | 1_3 | M | 2.3440 | 0.07598 |
| DAY*SEX | 3_5 | F | 2.0657 | 0.07865 |
| DAY*SEX | 3_5 | M | 2.0760 | 0.07598 |
| DAY*SEX | 5_7 | F | 1.9287 | 0.07598 |
| DAY*SEX | 5_7 | M | 2.2073 | 0.07598 |
| Lysine | | | | |
| DAY | 1_3 | | 0.6293 | 0.01142 |
| DAY | 3_5 | | 0.4857 | 0.01163 |
| DAY | 5_7 | | 0.4867 | 0.01142 |
| SEX | | F | 0.5327 | 0.009438 |
| SEX | | M | 0.5351 | 0.009328 |
| DAY*SEX | 1_3 | F | 0.6380 | 0.01616 |
| DAY*SEX | 1_3 | M | 0.6207 | 0.01616 |
| DAY*SEX | 3_5 | F | 0.4707 | 0.01672 |
| DAY*SEX | 3_5 | M | 0.5007 | 0.01616 |
| DAY*SEX | 5_7 | F | 0.4893 | 0.01616 |
| DAY*SEX | 5_7 | M | 0.4840 | 0.01616 |
| Citrate | | | | |
| DAY | 1_3 | | 0.2430 | 0.003706 |
| DAY | 3_5 | | 1.54E-17 | 0.003772 |
| DAY | 5_7 | | -147E-19 | 0.003706 |
| SEX | | F | 0.08400 | 0.003062 |
| SEX | | M | 0.07800 | 0.003026 |
| DAY*SEX | 1_3 | F | 0.2520 | 0.005241 |
| DAY*SEX | 1_3 | M | 0.2340 | 0.005241 |
| DAY*SEX | 3_5 | F | 1.61E-17 | 0.005425 |
| DAY*SEX | 3_5 | M | 1.47E-17 | 0.005241 |
| DAY*SEX | 5_7 | F | -282E-19 | 0.005241 |
| DAY*SEX | 5_7 | M | -13E-19 | 0.005241 |
| Pyruvate | | | | |
| DAY | 1_3 | | 0.4457 | 0.01806 |
| DAY | 3_5 | | 0.4812 | 0.01838 |
| DAY | 5_7 | | 0.3910 | 0.01806 |
| SEX | | F | 0.4137 | 0.01492 |
| SEX | | M | 0.4649 | 0.01474 |
| DAY*SEX | 1_3 | F | 0.4420 | 0.02554 |
| DAY*SEX | 1_3 | M | 0.4493 | 0.02554 |
| DAY*SEX | 3_5 | F | 0.4957 | 0.02643 |
| DAY*SEX | 3_5 | M | 0.4667 | 0.02554 |
| DAY*SEX | 5_7 | F | 0.3033 | 0.02554 |
| DAY*SEX | 5_7 | M | 0.4787 | 0.02554 |
| Methionine | | | | |
| DAY | 1_3 | | 0.1640 | 0.003429 |
| DAY | 3_5 | | 0.1279 | 0.003489 |
| DAY | 5_7 | | 0.1313 | 0.003429 |
| SEX | | F | 0.1379 | 0.002833 |
| SEX | | M | 0.1442 | 0.002800 |
| DAY*SEX | 1_3 | F | 0.1620 | 0.004849 |
| DAY*SEX | 1_3 | M | 0.1660 | 0.004849 |
| DAY*SEX | 3_5 | F | 0.1271 | 0.005019 |
| DAY*SEX | 3_5 | M | 0.1287 | 0.004849 |
| DAY*SEX | 5_7 | F | 0.1247 | 0.004849 |
| DAY*SEX | 5_7 | M | 0.1380 | 0.004849 |
| Acetate | | | | |
| DAY | 1_3 | | 0.5577 | 0.06009 |
| DAY | 3_5 | | 0.5679 | 0.06115 |
| DAY | 5_7 | | 0.7227 | 0.06009 |
| SEX | | F | 0.6219 | 0.04964 |
| SEX | | M | 0.6102 | 0.04906 |
| DAY*SEX | 1_3 | F | 0.5480 | 0.08498 |
| DAY*SEX | 1_3 | M | 0.5673 | 0.08498 |
| DAY*SEX | 3_5 | F | 0.6057 | 0.08796 |
| DAY*SEX | 3_5 | M | 0.5300 | 0.08498 |
| DAY*SEX | 5_7 | F | 0.7120 | 0.08498 |
| DAY*SEX | 5_7 | M | 0.7333 | 0.08498 |
| Leucine | | | | |
| DAY | 1_3 | | 0.7237 | 0.01749 |
| DAY | 3_5 | | 0.1937 | 0.01780 |
| DAY | 5_7 | | 0.1053 | 0.01749 |
| SEX | | F | 0.3287 | 0.01445 |
| SEX | | M | 0.3531 | 0.01428 |
| DAY*SEX | 1_3 | F | 0.7160 | 0.02473 |
| DAY*SEX | 1_3 | M | 0.7313 | 0.02473 |
| DAY*SEX | 3_5 | F | 0.1907 | 0.02560 |
| DAY*SEX | 3_5 | M | 0.1967 | 0.02473 |
| DAY*SEX | 5_7 | F | 0.07933 | 0.02473 |
| DAY*SEX | 5_7 | M | 0.1313 | 0.02473 |
| Alanine | | | | |
| DAY | 1_3 | | 0.2530 | 0.02296 |
| DAY | 3_5 | | 0.1367 | 0.02337 |
| DAY | 5_7 | | 0.1287 | 0.02296 |
| SEX | | F | 0.1554 | 0.01897 |
| SEX | | M | 0.1902 | 0.01875 |
| DAY*SEX | 1_3 | F | 0.2260 | 0.03248 |
| DAY*SEX | 1_3 | M | 0.2800 | 0.03248 |
| DAY*SEX | 3_5 | F | 0.1321 | 0.03362 |
| DAY*SEX | 3_5 | M | 0.1413 | 0.03248 |
| DAY*SEX | 5_7 | F | 0.1080 | 0.03248 |
| DAY*SEX | 5_7 | M | 0.1493 | 0.03248 |
| Valine | | | | |
| DAY | 1_3 | | 0.4430 | 0.01967 |
| DAY | 3_5 | | 0.4517 | 0.02002 |
| DAY | 5_7 | | 0.4477 | 0.01967 |
| SEX | | F | 0.3967 | 0.01625 |
| SEX | | M | 0.4982 | 0.01606 |
| DAY*SEX | 1_3 | F | 0.3280 | 0.02782 |
| DAY*SEX | 1_3 | M | 0.5580 | 0.02782 |
| DAY*SEX | 3_5 | F | 0.4507 | 0.02880 |
| DAY*SEX | 3_5 | M | 0.4527 | 0.02782 |
| DAY*SEX | 5_7 | F | 0.4113 | 0.02782 |
| DAY*SEX | 5_7 | M | 0.4840 | 0.02782 |
| Isoleucine | | | | |
| DAY | 1_3 | | 0.4257 | 0.01821 |
| DAY | 3_5 | | 0.4039 | 0.01853 |
| DAY | 5_7 | | 0.3893 | 0.01821 |
| SEX | | F | 0.3581 | 0.01504 |
| SEX | | M | 0.4544 | 0.01487 |
| DAY*SEX | 1_3 | F | 0.3200 | 0.02575 |
| DAY*SEX | 1_3 | M | 0.5313 | 0.02575 |
| DAY*SEX | 3_5 | F | 0.3957 | 0.02666 |

TABLE 3-continued

Mean and standard error by effects for each metabolite and interaction

| Effect | DAY | SEX | Estimate | Standard Error |
|---|---|---|---|---|
| DAY*SEX | 3_5 | M | 0.4120 | 0.02575 |
| DAY*SEX | 5_7 | F | 0.3587 | 0.02575 |
| DAY*SEX | 5_7 | M | 0.4200 | 0.02575 |

However, histidine, pyruvate, valine, and isoleucine changed their pattern across period and gender suggesting that these variables in isolation can be predictors of gender (FIG. 5A and FIG. 5B and FIG. 6A and FIG. 6B).

Figure 7:
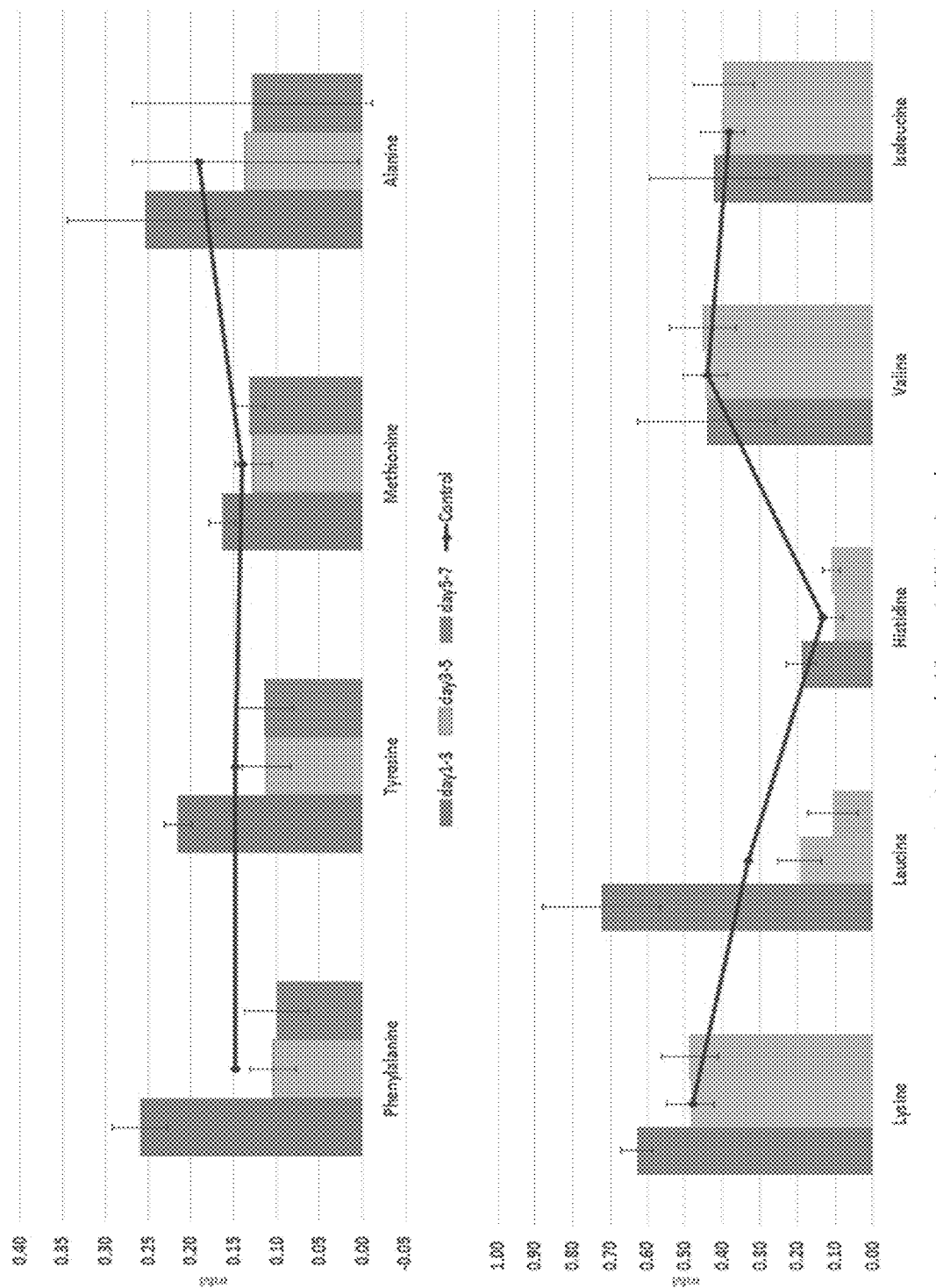
FIG. 7 are graphs showing amino acid metabolism during different phases of development. The line shows the value of the amino acids (phenylalanine, tyrosine, methionine, alanine, lysine, leucine, histidine, valine and isoleucine) in the medium before the embryo incubation.
Figure 8:
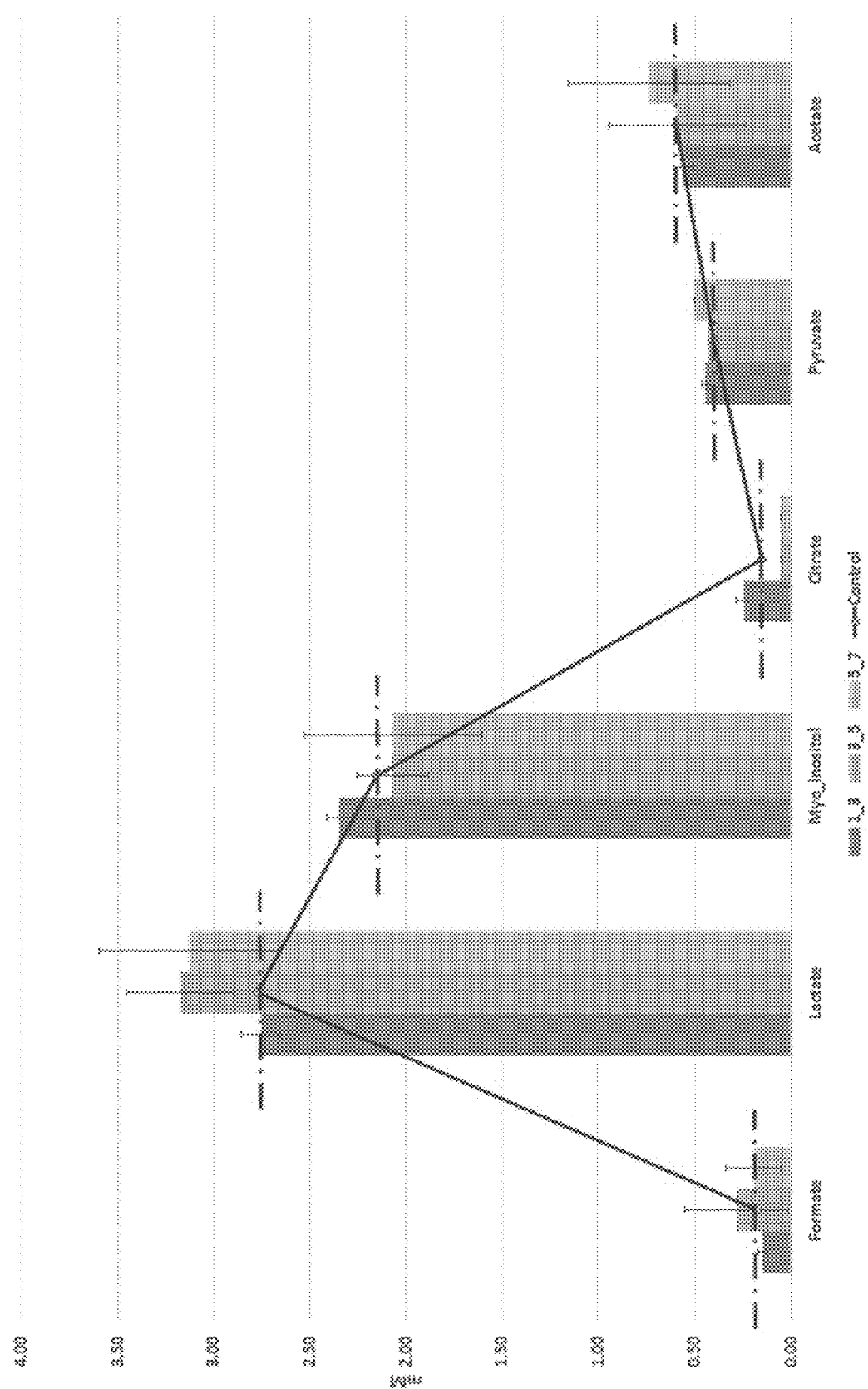
FIG. 8 is a graph showing sugar metabolism during different phases of development. The line shows the value of the sugars (formate, lactate, myo-inositol, citrate, pyruvate and acetate) in the medium before the embryo incubation.

The changes across time periods for metabolites with significant interaction showed changes in the slopes (FIG. 7 and FIG. 8). For example, isoleucine and valine presented different values between males and females in the early period; however, in the middle and late periods, they presented more similar values indicating that valine and isoleucine can be a predictive variable of gender in the early period (days 1-3). Pyruvate showed the opposite trend, with similar values in the early and middle time periods and different values in the late time period. Based on these results, an analysis of the metabolites in each time period was undertaken using logistic regression. The data from all the embryos analyzed in the early period by logistic regression are presented in Table 4.

TABLE 4

Univariate analysis of individual predictors (standardized) by logistic regression detailing coefficient estimates, levels of significance and odds ratio ± 95% in the early (days 1-3) period

| Potential predictor | Estimate | Standard Error (SE) | P-value | Odds ratio | 95% Confidence limits (CI) | |
|---|---|---|---|---|---|---|
| Formate | −0.0339 | 0.3717 | 0.9274 | 0.967 | 0.467 | 2.003 |
| Phenylalanine | 0.2142 | 0.3799 | 0.5729 | 1.239 | 0.588 | 2.609 |
| Histidine | 1.8011 | 1.0362 | 0.0822 | 6.056 | 0.795 | 46.153 |
| Tyrosine | 1.0107 | 0.6456 | 0.1174 | 2.748 | 0.775 | 9.737 |
| Lactate | −1.2029 | 0.5741 | 0.0362 | 0.300 | 0.097 | 0.925 |
| Lysine | 0.4629 | 0.3910 | 0.2365 | 1.589 | 0.738 | 3.418 |
| Citrate | 0.6469 | 0.5047 | 0.2000 | 1.910 | 0.710 | 5.135 |
| Pyruvate | −0.4661 | 0.3878 | 0.2294 | 0.627 | 0.293 | 1.342 |
| Methionine | −0.3068 | 0.3843 | 0.4246 | 0.736 | 0.346 | 1.563 |
| Acetate | −0.3903 | 0.3889 | 0.3156 | 0.677 | 0.316 | 1.451 |
| Leucine | −0.1149 | 0.3774 | 0.7609 | 0.891 | 0.425 | 1.868 |
| Isoleucine | −3.8753 | 1.5794 | 0.0141 | 0.021 | <0.001 | 0.459 |
| Alanine | −0.7767 | 0.5474 | 0.1559 | 0.460 | 0.157 | 1.345 |
| Valine | −4.7447 | 2.2544 | 0.0353 | 0.009 | <0.001 | 0.722 |

Although lactate, isoleucine and valine showed a significant P-value in the univariate analysis, only valine remained significant when the stepwise selection was performed and presented a predictive index. This metabolite correctly predicts the gender of the embryo 66.7% of the time with a sensitivity of 60% and specificity of 73% (Table 5).

Likewise, an analysis of the middle time period was undertaken. The univariate analysis indicated that none of the variables were significant (Table 6).

TABLE 6

Univariate analysis of individual predictors (standardized) by logistic regression detailing coefficient estimates, levels of significance and odds ratio ± 95% in the middle (days 3-5) period

| Potential predictor | Estimate | Standard Error (SE) | P-value | Odds ratio | 95% Confidence limits (CI) | |
|---|---|---|---|---|---|---|
| Formate | 0.7571 | 0.5280 | 0.1516 | 2.132 | 0.758 | 6.001 |
| Phenylalanine | −0.2508 | 0.3880 | 0.5180 | 0.778 | 0.364 | 1.665 |
| Histidine | 0.3500 | 0.3861 | 0.3646 | 1.419 | 0.666 | 3.025 |
| Tyrosine | −0.0759 | 0.3801 | 0.8417 | 0.927 | 0.440 | 1.952 |
| Lactate | 0.0317 | 0.3781 | 0.9332 | 1.032 | 0.492 | 2.166 |
| Myo-Insoitol | −0.0549 | 0.3794 | 0.8849 | 0.947 | 0.450 | 1.991 |
| Lysine | −0.4827 | 0.4106 | 0.2398 | 0.617 | 0.276 | 1.380 |
| Pyruvate | 0.5205 | 0.4331 | 0.2294 | 1.683 | 0.720 | 3.933 |
| Methionine | −0.0652 | 0.3794 | 0.8635 | 0.937 | 0.445 | 1.971 |
| Acetate | 0.2242 | 0.3809 | 0.5561 | 1.251 | 0.593 | 2.640 |
| Leucine | −0.1045 | 0.3801 | 0.7835 | 0.901 | 0.428 | 1.898 |
| Isoleucine | −0.2850 | 0.3980 | 0.4741 | 0.752 | 0.345 | 1.641 |
| Alanine | −0.0693 | 0.3785 | 0.8547 | 0.933 | 0.444 | 1.959 |
| Valine | −0.0309 | 0.3790 | 0.9350 | 0.970 | 0.461 | 2.038 |

The stepwise selection in the multi-regression logistic model corroborated the previous findings where none of the variables were selected, suggesting that these variables were unable to correctly classify the gender of the embryo.

Figure 5A:
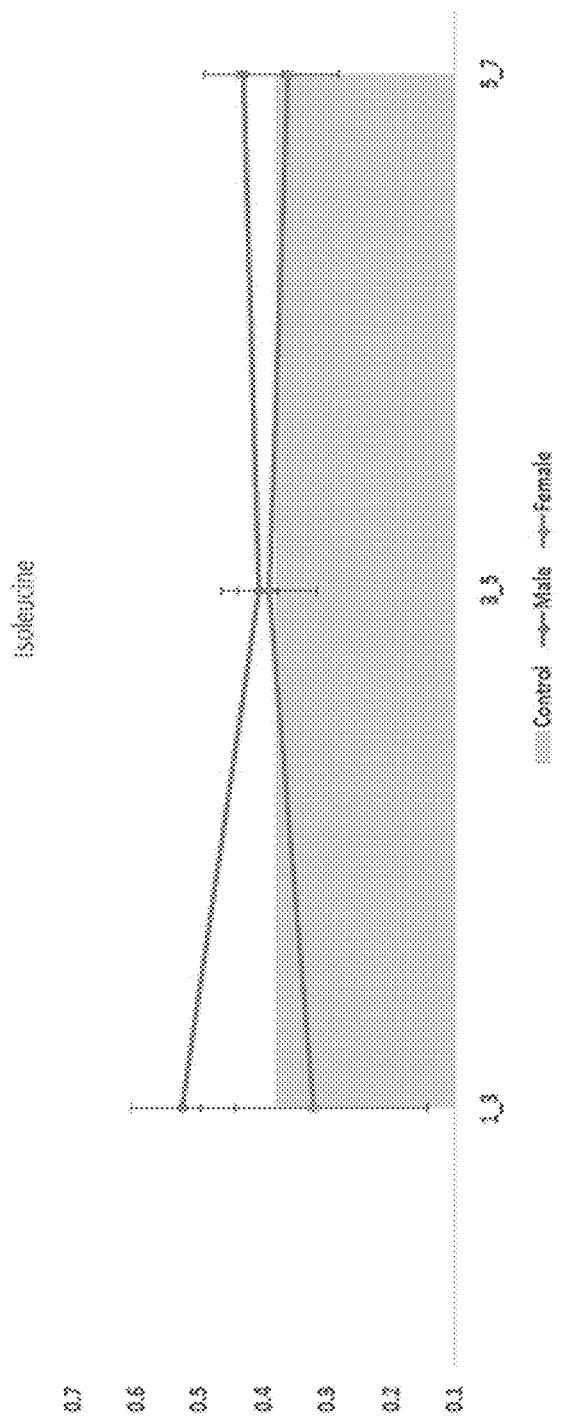
FIG. 5A-5B shows isoleucine and histidine changes during embryo development.
Figure 5B:
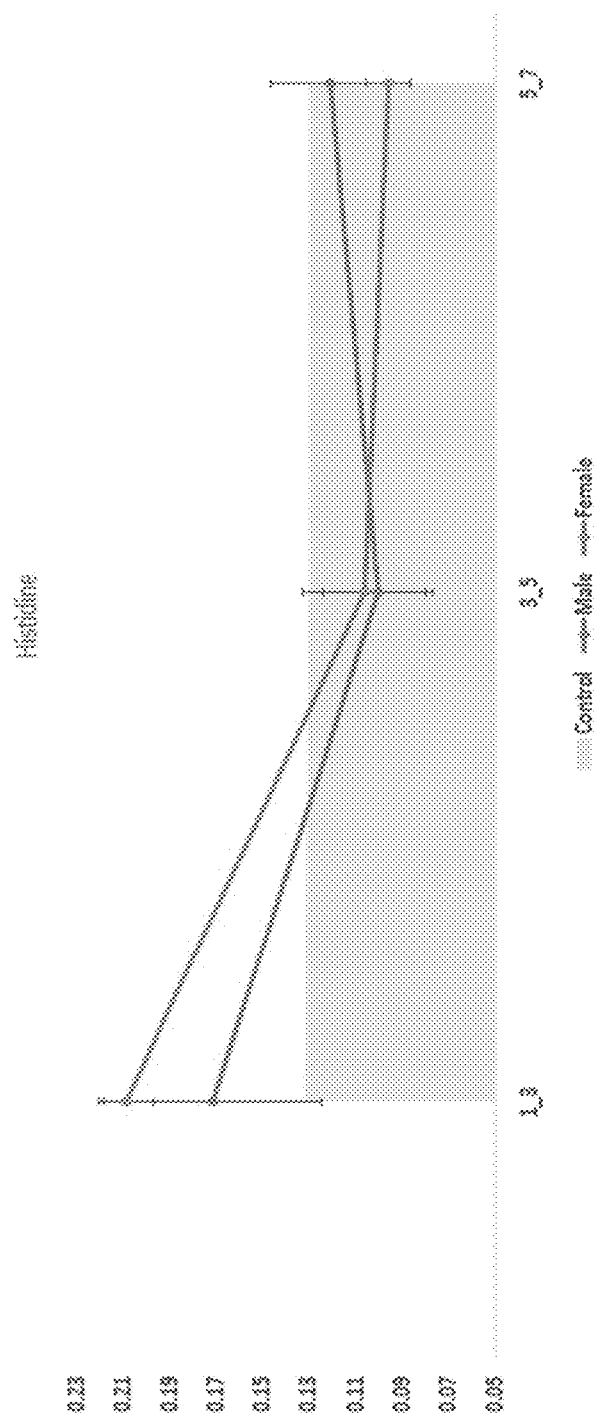
Figure 6A:
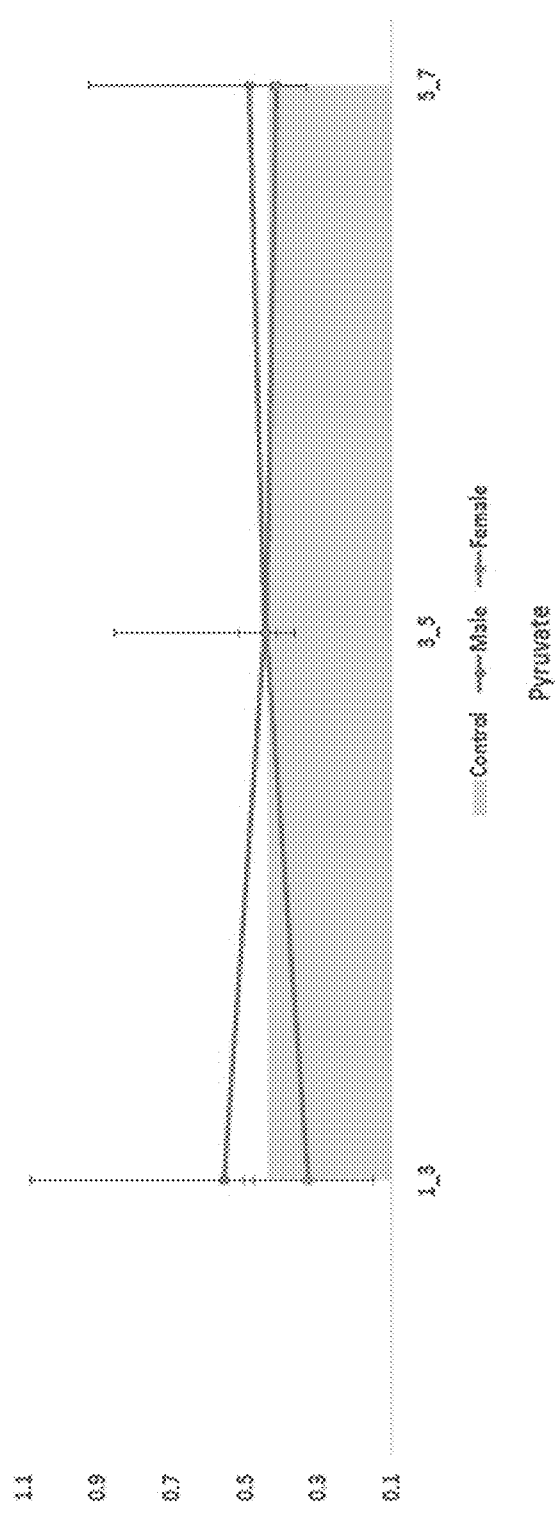
FIG. 6A-6B shows valine and pyruvate changes during embryo development.
Figure 6B:
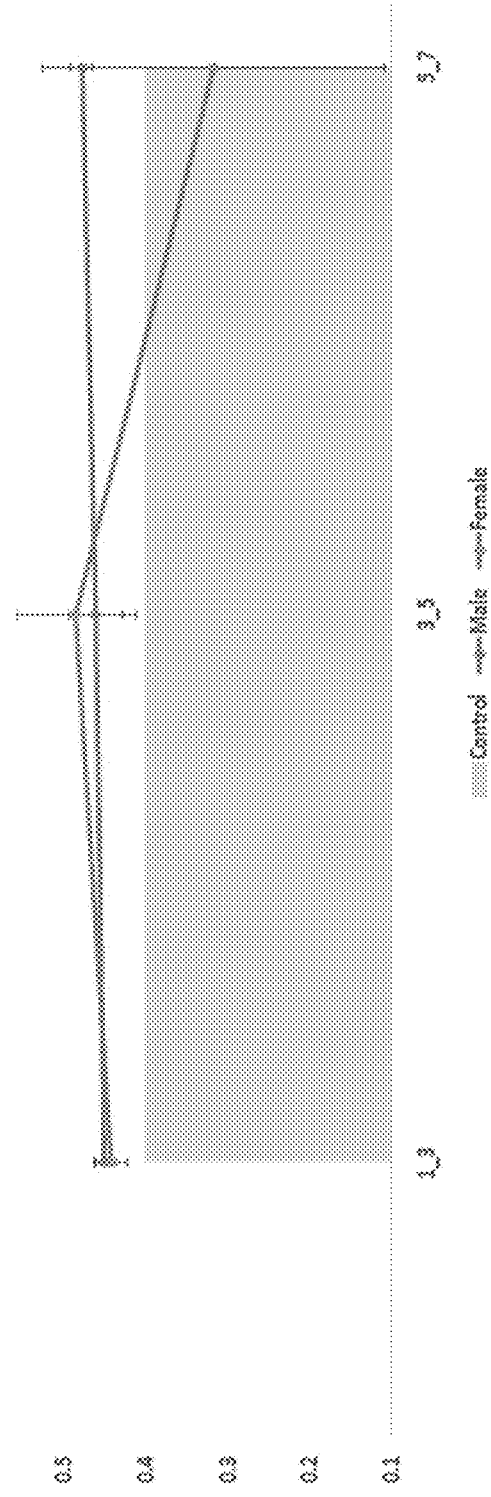

Finally, an analysis was performed for the late time period (day 5-7). Although histidine, pyruvate, and isoleucine showed a significant P-value (Table 7) in the univariate analysis, only pyruvate remained when the stepwise selection was performed and presented a predictive index (FIGS. 5A-5B).

TABLE 7

Univariate analysis of individual predictors (standardized) by logistic regression detailing coefficients estimates, levels of significance and odds ratio ± 95% in the late (days 5-7) period.

| Potential predictor | Estimate | Standard Error (SE) | P-value | Odds ratio | 95% Confidence limits (CI) | |
|---|---|---|---|---|---|---|
| Formate | −0.1767 | 0.3736 | 0.6361 | 0.838 | 0.403 | 1.743 |
| Phenylalanine | −0.3368 | 0.3964 | 0.3956 | 0.714 | 0.328 | 1.553 |
| Histidine | −1.0921 | 0.4891 | 0.0256 | 0.336 | 0.129 | 0.875 |
| Tyrosine | −0.7944 | 0.4690 | 0.0903 | 0.452 | 0.180 | 1.133 |
| Lactate | −0.2882 | 0.3826 | 0.4512 | 0.750 | 0.354 | 1.587 |

TABLE 5

Classification of the prediction variable, valine, in the early (days 1-3) period

| | Absolute value | | | | Percentages | | | |
|---|---|---|---|---|---|---|---|---|
| | Correct | | Incorrect | | | | False | False |
| Metabolite | ♀ | ♂ | ♀ | ♂ | Correct | Sensitivity | Specificity | POS | NEG |
| Valine | 9 | 11 | 4 | 6 | 66.7 | 60.0 | 73.3 | 30.8 | 35.3 |

False POS false positive, false NEG false negative

TABLE 7-continued

Univariate analysis of individual predictors (standardized) by logistic regression detailing coefficients estimates, levels of significance and odds ratio ± 95% in the late (days 5-7) period.

| Potential predictor | Estimate | Standard Error (SE) | P-value | Odds ratio | 95% Confidence limits (Cl) | |
|---|---|---|---|---|---|---|
| Myo-Insoitol | −0.6649 | 0.4281 | 0.1204 | 0.514 | 0.222 | 1.190 |
| Lysine | −0.0748 | 0.3721 | 0.8407 | 1.078 | 0.520 | 2.235 |
| Pyruvate | −1.4630 | 0.6995 | 0.0365 | 0.232 | 0.059 | 0.912 |
| Methionine | −1.0304 | 0.5460 | 0.0591 | 0.357 | 0.122 | 1.041 |
| Acetate | −0.0507 | 0.3715 | 0.8915 | 0.951 | 0.459 | 1.969 |
| Leucine | −0.9431 | 0.4463 | 0.0346 | 0.389 | 0.162 | 0.934 |
| Isoleucine | −0.9567 | 0.5193 | 0.0654 | 0.384 | 0.139 | 1.063 |
| Alanine | −0.3064 | 0.3759 | 0.4150 | 0.736 | 0.352 | 1.538 |
| Valine | −1.2087 | 0.6750 | 0.0734 | 0.299 | 0.080 | 1.121 |

Pyruvate predicts the gender of the embryo correctly 64.7% of the time with a sensitivity of 40% and specificity of 80% (Table 8).

TABLE 8

Classification of the prediction variable pyruvate in the late (days 5-7) period.

| | Absolute value | | | | Percentages | | | | |
|---|---|---|---|---|---|---|---|---|---|
| | Correct | | Incorrect | | | | | False | False |
| Metabolite | ♀ | ♂ | ♀ | ♂ | Correct | Sensitivity | Specificity | POS | NEG |
| Pyruvate | 4 | 12 | 3 | 6 | 64.0 | 40.0 | 80.0 | 42.9 | 33.3 |

False POS false positive, false NEG false negative

Metabolic parameters can be a marker of embryo viability. This stems from the fact that metabolism is fundamental to early embryo health and is immediately perturbed when embryos are stressed. These results demonstrate that spent embryo culture media from viable and non-viable embryos differ in their metabolite composition, thus making media assessment a potential non-invasive method for the selection of embryos. Furthermore, such analyses can be used to characterize embryo metabolic behavior. In this study, 1H NMR was used for the first time to compare the differences in metabolic behavior between male and female bovine embryos cultured in single drops and to evaluate different time points of embryo development. The entire pool of metabolites evaluated gave a complete view of metabolism for the two sexes during development.

Example 2: Determining the Gender of an Embryo Based on Changes in Metabolites To better understand the metabolism, the dataset of all embryos was first evaluated to help follow the dynamic change in each metabolite. This analysis shows that all amino acids evaluated follow the same trend: the consumption increases after day 3. In the first phase of development, zygotes derive their energetic substrates from substrates contained within themselves. However, the sugar consumption is different for each sugar over time. Myo-inositol and citrate concentrations decrease during development while pyruvate consumption/production is constant for the entire embryo culture. These sugar modulations are evidence that metabolism is slower in the first 2 days of development because the zygotes use their internal lipid reserves. Formate metabolism changes based on the stage of development: the maximum concentration was found at days 3-5 when the Krebs cycle is in full activity. This modulation is explained in that formate is important for purine synthesis, which occurs after a couple of days of development when the embryos start their own DNA biosynthesis. The lactate concentration increases after day 3 of culture.

Figure 9:
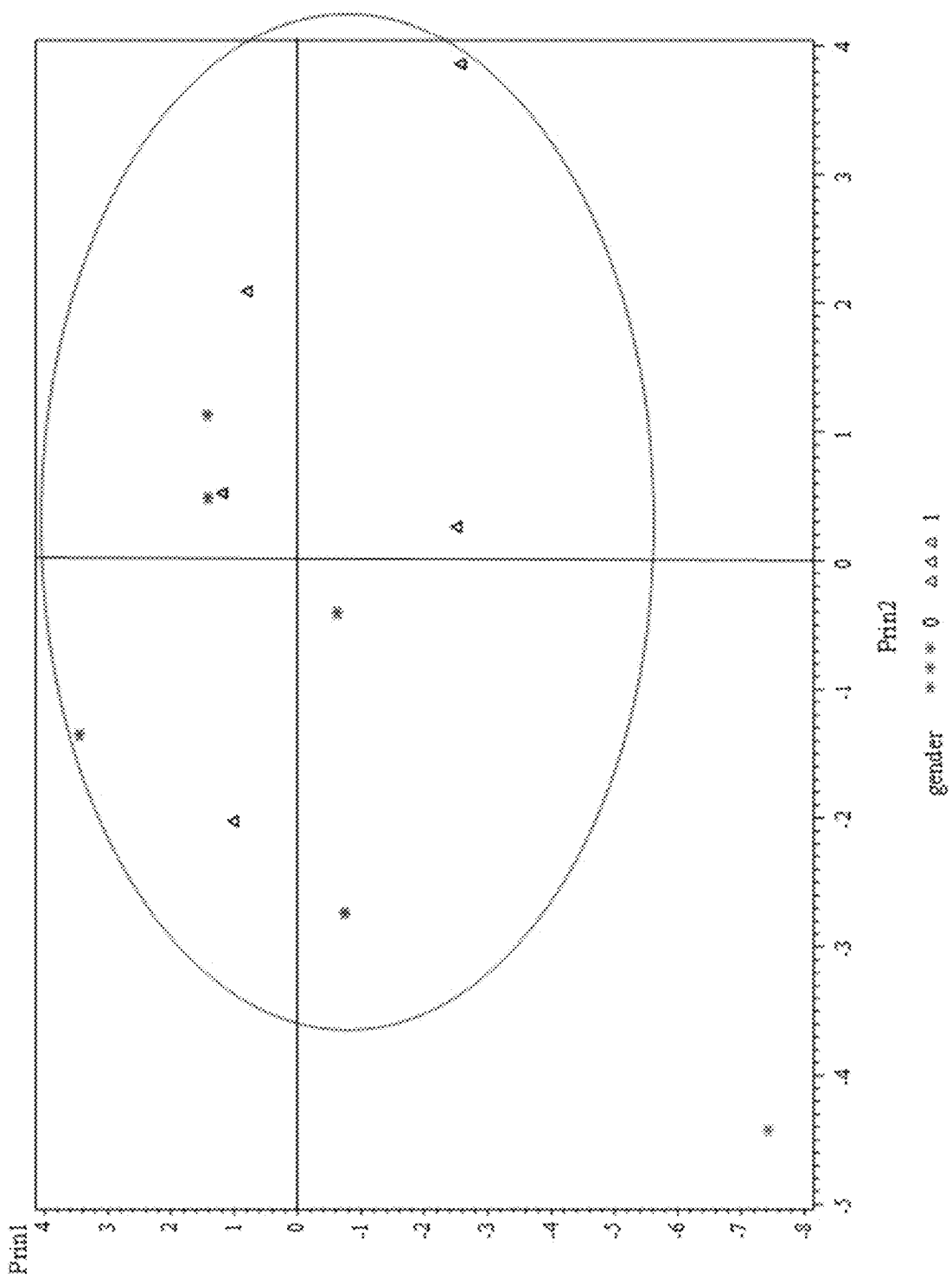
FIG. 9 is a plot of the first two principal components of the early days (1-3) of development: 0=Male Embryos; 1=Female Embryos.
Figure 10:
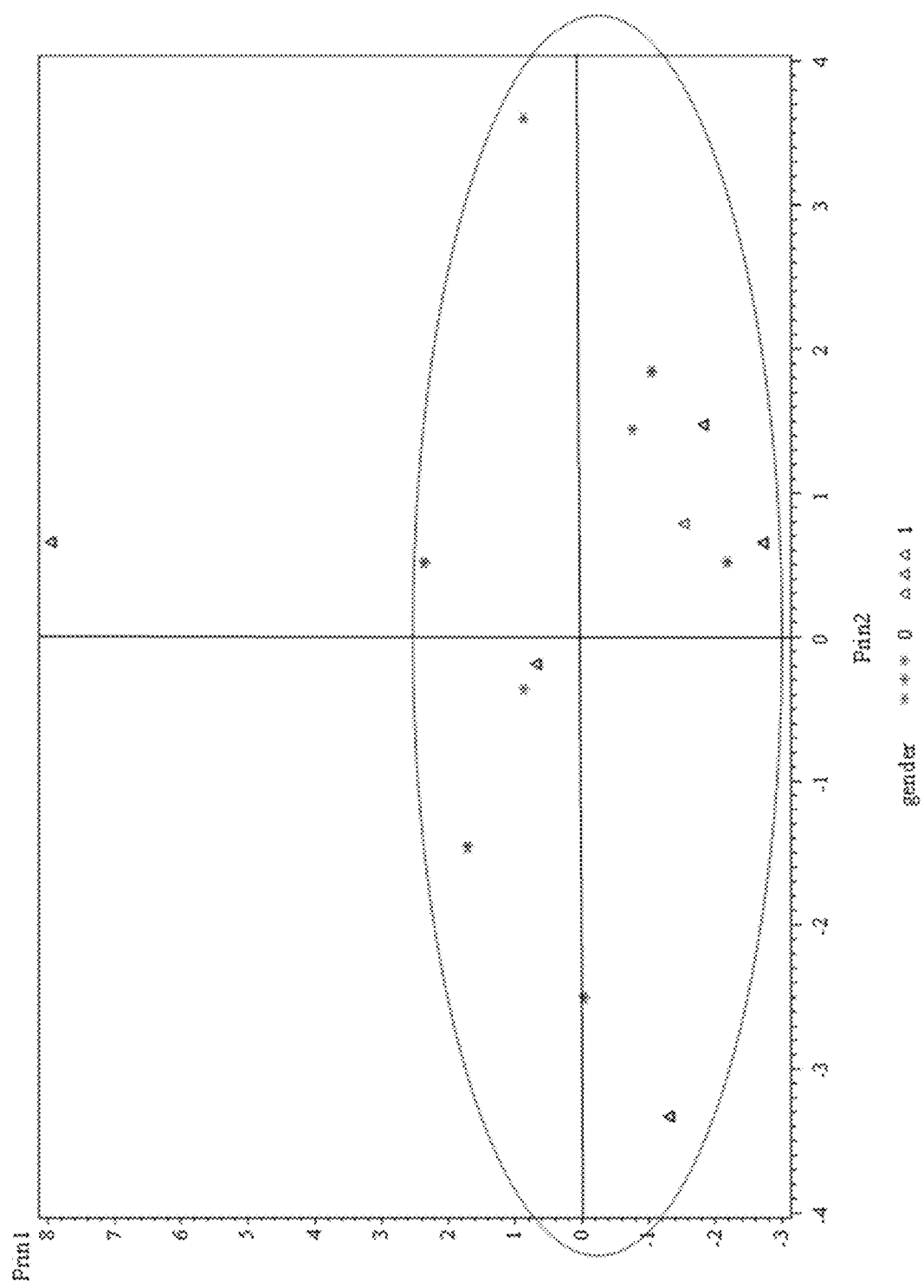
FIG. 10 is a plot of the first two principal components of the middle days (3-5) of development: 0=Male Embryos; 1=Female Embryos.
Figure 11:
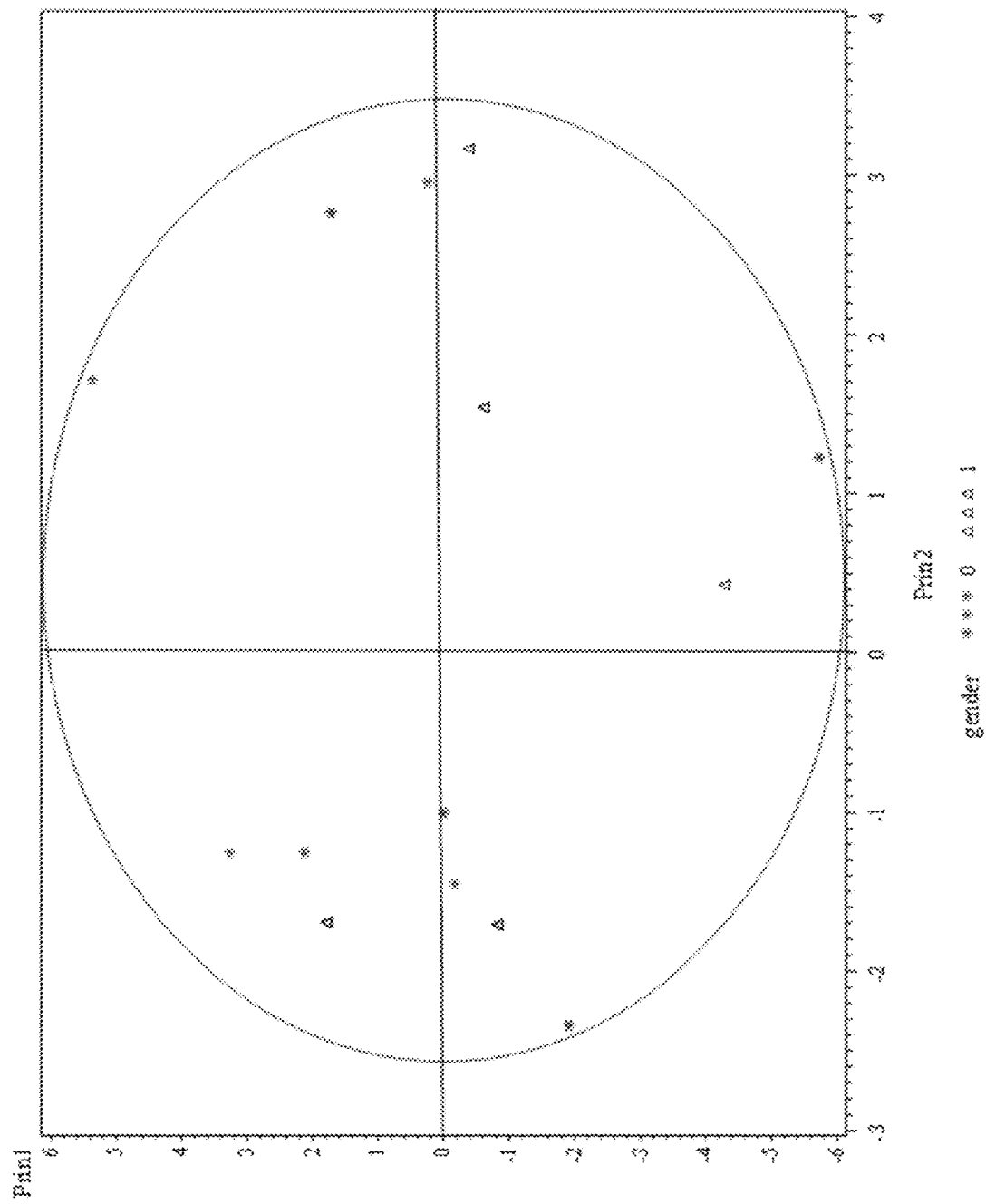
FIG. 11 is a plot of the first two principal components of the late days (5-7) of development: 0=Male Embryos; 1=Female Embryos.

In the second phase of the evaluation, PCA between sexes during the three time periods were compared (FIG. 9, FIG. 10, and FIG. 11 demonstrate the relationship between metabolites and their changes across time). PCA is a data mining technique that reduces the redundancy among variables creating uncorrelated features called principal components with minimum information loss, keeping as much variability in the data as possible, and enabling visualization of observations. For this particular experiment no additional information was gained using this technique and the sex was not dominated for any particular eigen value. In the last phase of the evaluation, each metabolite between sexes during the different periods of development was compared. Metabolite modulation with relative differences>20% between sexes and statistically significant differences were considered. In the first days of development only valine and isoleucine had a statistically significant difference and were beyond the base line, of these two, only valine can be used as a marker for gender evaluation (FIGS. 5A-5B and FIGS. 6A-6B).

The results showed that for each additional unit of valine found in the medium, there is a 58% increased probability that the embryo will be male (Table 9), which indicates that it is a suitable marker to predict gender.

TABLE 9

Valine Probability to be female or male

| Value of Valine (mM) | 0.1 | 0.2 | 0.3 | 0.4 | 0.5 | 0.6 | 0.7 | 0.8 | 0.9 | 1 |
|---|---|---|---|---|---|---|---|---|---|---|
| Probability to be a Female | 71% | 60% | 48% | 37% | 26% | 18% | 12% | 8% | 5% | 3% |
| Probability to be a Male | 30% | 40% | 52% | 63% | 74% | 82% | 88% | 92% | 95% | 97% |

The results suggest valine is consumed more by female than male embryos. The analysis also showed that during the middle of embryo culture, when the X chromosome is inactivated, there are no statistical differences between sexes, meaning that during this phase of development there is a similarity in the metabolism between sexes. During the period of development when morulas become blastocysts, pyruvate turnover is different between sexes. The results showed that it is also possible to use pyruvate as a marker to predict the gender of the embryos. It was found that for each additional unit of pyruvate, found in the media, there is a 25% increased probability that embryos will be male (Table 10).

TABLE 10

Pyruvate probability to be female or male

| Pyruvate Value (mM) | 0.1 | 0.2 | 0.3 | 0.4 | 0.5 | 0.6 | 0.7 | 0.8 | 0.9 | 1 |
|---|---|---|---|---|---|---|---|---|---|---|
| Probability to be a Female | 37% | 34% | 30% | 27% | 25% | 22% | 20% | 17% | 15% | 14% |
| Probability to be a Male | 63% | 66% | 70% | 73% | 75% | 78% | 80% | 83% | 85% | 86% |

These pyruvate values from days 5-7 are able to predict the embryo's sex with an accuracy of 64% (Table 8).

In conclusion, the results described herein confirm that embryo metabolism is different between sexes, and there are at least three important steps for metabolic behavior during embryo development: (1) before the embryonic genome is established (2) intermediate phase when there are a high cleavage phase and (3) formation of blastocysts. The new information obtained by, for example, 1H NMR identifies markers that can be used to predict the embryo's sex. These results open a new, non-invasive method to evaluate sex of the embryos before the transfer.

In the first period of embryo culture, the valine concentration is a good indicator (66.7% accurate), while in the last phase of culture, the pyruvate depletion is a good marker (64% accurate) to evaluate the sex of the embryo. Individual embryo culture does not affect blastocyst yield if carried out in the last phase of development, however, single embryo culture during the first phase (day 1-3) of development decreases the blastocyst rate (approximately 4-7%). Pyruvate can be a marker for sex evaluation in procedures, such as NMR procedures at later culture stages (day 5-7). The ability to non-invasively assess the gender of an embryo before the transfer can help meet the demands for known sex offspring while maintaining in vitro culture conditions that produce blastocysts with acceptable efficiency.

We claim:

1. A method for determining the gender of an embryo, the method comprising:
   (i) growing an embryo in an in vitro culture media; and
   (ii) identifying the amount of valine, pyruvate, or both valine and pyruvate contained in the spent culture media during early development, late development, or a combination thereof; wherein the presence of valine during early development in a concentration above a baseline indicates that the embryo will more likely be male than female, and the presence of pyruvate during late development in a concentration above a baseline indicates that the embryo will more likely be male than female; and
   (iii) selecting an embryo based on a likely gender and implanting the embryo into a uterus.

2. The method of claim 1, wherein early development is about 24 hours to about 72 hours after a zygote is formed.

3. The method of claim 1, wherein late development is about 120 hours to about 168 hours after a zygote is formed.

4. The method of claim 1, wherein the embryo is a mammalian embryo.

5. The method of claim 1, wherein the embryo is a human embryo, bovine embryo, a porcine embryo, an equine embryo, an ovine embryo, a hircine embryo, a canine embryo, a feline embryo, a murine embryo, a rabbit embryo, or a rodent embryo.

6. The method of claim 1, wherein the gender of the embryo is determined before the embryo is transferred into an animal.

7. The method of claim 6, wherein the animal is a human, cow, pig, horse, sheep, goat, dog, cat, mouse, rat, or rabbit.

8. The method of claim 1, wherein the presence of valine during early development in a concentration below or about a baseline indicates that the embryo will more likely be female than male.

9. The method of claim 1, wherein the presence of pyruvate during late development in a concentration at about or below a base line indicates that the embryo will more likely be female than male.

10. The method of claim 1, wherein the amounts of pyruvate and valine are identified by nuclear magnetic resonance, high performance liquid chromatography, gas chromatography, or mass spectroscopy.

11. The method of claim 1, wherein the amount of pyruvate or valine indicates the gender of the embryo with an accuracy of over 60%.

* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: bSRY A

<400> SEQUENCE: 1

```
acagtcatag cgcaaatgat cagtg                                              25

<210> SEQ ID NO 2
<211> LENGTH: 26
<212> TYPE: DNA
<213> ORGANISM: Artificial Sequence
<220> FEATURE:
<223> OTHER INFORMATION: bSRY 1

<400> SEQUENCE: 2
gggttgcata gtattgaaga gtctgc                                             26

<210> SEQ ID NO 3
<211> LENGTH: 26
<212> TYPE: DNA
<213> ORGANISM: Artificial Sequence
<220> FEATURE:
<223> OTHER INFORMATION: btRep-137 C1

<400> SEQUENCE: 3
tattttcgga acgcgggaga gaagag                                             26

<210> SEQ ID NO 4
<211> LENGTH: 29
<212> TYPE: DNA
<213> ORGANISM: Artificial Sequence
<220> FEATURE:
<223> OTHER INFORMATION: btRep-137 C2

<400> SEQUENCE: 4
tatttttgat tccctccgtg cggcgctta                                          29
```